(12) United States Patent
Churcher et al.

(10) Patent No.: US 6,995,155 B2
(45) Date of Patent: Feb. 7, 2006

(54) BENZODIAZEPINE DERIVATIVES AS INHIBITORS OF GAMMA SECRETASE

(75) Inventors: Ian Churcher, Great Dunmow (GB); Alan John Nadin, Sawbridgeworth (GB); Andrew Pate Owens, Huntingdon (GB)

(73) Assignee: Merck Sharp & Dohme Limited, Hoddesdon (GB)

( * ) Notice: Subject to any disclaimer, the term of this patent is extended or adjusted under 35 U.S.C. 154(b) by 283 days.

(21) Appl. No.: 10/399,231

(22) PCT Filed: Aug. 8, 2001

(86) PCT No.: PCT/GB01/04474

§ 371 (c)(1),
(2), (4) Date: Apr. 11, 2003

(87) PCT Pub. No.: WO02/30912

PCT Pub. Date: Apr. 18, 2002

(65) Prior Publication Data

US 2004/0024203 A1    Feb. 5, 2004

(30) Foreign Application Priority Data

Oct. 13, 2000    (GB) ................................. 0025173

(51) Int. Cl.
| | | |
|---|---|---|
| *C07D 243/24* | (2006.01) | |
| *C07D 403/04* | (2006.01) | |
| *A61K 31/5513* | (2006.01) | |
| *A61P 25/28* | (2006.01) | |

(52) U.S. Cl. ...................................... 514/221; 540/509
(58) Field of Classification Search ................ 540/509; 514/221

See application file for complete search history.

(56) References Cited

U.S. PATENT DOCUMENTS

2004/0082572 A1    4/2004    Pineiro et al.

FOREIGN PATENT DOCUMENTS

| WO | WO 95 14471 A | 6/1995 |
| WO | WO 98 28268 A | 7/1998 |
| WO | WO 00 14073 A | 3/2000 |
| WO | WO 00 38618 A | 7/2000 |

*Primary Examiner*—Bruck Kifle
(74) *Attorney, Agent, or Firm*—John C. Todaro; Melvin Winokur

(57) ABSTRACT

Compounds of formula (I) are disclosed. The compounds inhibit the action of gamma secretase, and hence find use in the treatment and prevention of Alzheimer's disease.

8 Claims, No Drawings

BENZODIAZEPINE DERIVATIVES AS INHIBITORS OF GAMMA SECRETASE

CROSS REFERENCE TO RELATED APPLICATIONS

This application is a U.S. National Phase application under 35 U.S.C. § 371 of PCT Application No. PCT/GB01/04474, filed Oct. 8, 2001, which claims priority under 35 U.S.C. § 119 from GB Application No. 0025173.6, filed Oct. 13, 2000.

The present invention relates to a novel class of compounds, their salts, pharmaceutical compositions comprising them, processes for making them and their use in therapy of the human body. In particular, the invention relates to compounds which modulate the processing of APP by γ-secretase, and hence are useful in the treatment or prevention of Alzheimer's disease.

Alzheimer's disease (AD) is the most prevalent form of dementia. Although primarily a disease of the elderly, affecting up to 10% of the population over the age of 65, AD also affects significant numbers of, younger patients with a genetic predisposition. It is a neurodegenerative disorder, clinically characterized by progressive loss of memory and cognitive function, and pathologically characterized by the deposition of extracellular proteinaceous plaques in the cortical and associative brain regions of sufferers. These plaques mainly comprise fibrillar aggregates of β-amyloid peptide (Aβ), and although the exact role of the plaques in the onset and progress of AD is not fully understood, it is generally accepted that suppressing or attenuating the secretion of Aβ is a likely means of alleviating or preventing the condition. (See, for example, *ID research alert* 1996 1(2): 1–7; *ID research alert* 1997 2(1):1–8; *Current Opinion in CPNS Investigational Drugs* 1999 1(3):327–332; and *Chemistry in Britain*, January 2000, 28–31.)

Aβ is a peptide comprising 39–43 amino acid residues, formed by proteolysis of the much larger amyloid precursor protein. The amyloid precursor protein (APP or AβPP) has a receptor-like structure with a large ectodomain, a membrane spanning region and a short cytoplasmic tail. Different isoforms of APP result from the alternative splicing of three exons in a single gene and have 695, 751 and 770 amino acids respectively.

The Aβ domain encompasses parts of both extra-cellular and transmembrane domains of APP, thus its release implies the existence of two distinct proteolytic events to generate its $NH_2$— and COOH-termini. At least two secretory mechanisms exist which release APP from the membrane and generate the soluble, COOH-truncated forms of APP ($APP_s$). Proteases which release APP and its fragments from the membrane are termed "secretases". Most $APP_s$ is released by a putative α-secretase which cleaves within the Aβ domain (between residues $Lys^{16}$ and $Leu^{17}$) to release α-$APP_s$ and precludes the release of intact Aβ. A minor portion of $APP_s$ is released by a β-secretase, which cleaves near the $NH_2$-terminus of Aβ and produces COOH-terminal fragments (CTFs) which contain the whole Aβ domain. Finding these fragments in the extracellular compartment suggests that another proteolytic activity (γ-secretase) exists under normal conditions which can generate the COOH-terminus of Aβ.

It is believed that γ-secretase itself depends for its activity on the presence of presenilin-1. In a manner that is not fully understood, full length presenilin-1 undergoes cleavage to a C-terminal fragment and an N-terminal fragment.

There are relatively few reports in the literature of compounds with inhibitory activity towards β- or γ-secretase, as measured in cell-based assays. These are reviewed in the articles referenced above. Many of the relevant compounds are peptides or peptide derivatives.

WO95/14471 and WO95/14676 disclose classes of 3-acylaminobenzodiazepines which are antiarrhythmic agents, but do not disclose inhibition of γ-secretase.

WO98/28268 discloses a broad range of compounds as inhibitors of γ-secretase, including certain 3-acylamino-5-aryl-1,4-benzodiazepines, but there is no disclosure of compounds in accordance with the present invention.

According to the invention, there is a provided a compound of formula I:

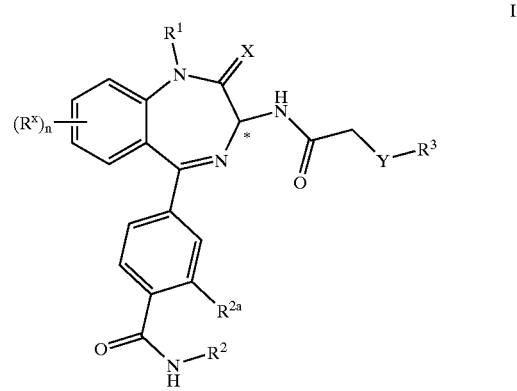

wherein:

n is 0–3;

each $R^x$ independently represents halogen, —CN, —$NO_2$, $C_{1-6}$alkyl, polyfluoro$C_{1-6}$alkyl, —OH or $C_{1-4}$alkoxy;

X represents O, S or N—$R^a$ where $R^a$ together with $R^1$ completes a fused imidazole or 4,5-dihydroimidazole ring;

Y represents —$CH_2$—, —CH(OH)—, —CH($CH_3$)—, —$CH_2$O—, —O— or —S;

$R^1$ represents H, $C_{1-6}$alkyl, $C_{3-8}$cycloalkyl, $C_{2-6}$alkyl, $C_{2-6}$alkynyl or polyfluoro$C_{1-6}$alkyl, said alkyl, cycloalkyl, alkenyl and alkynyl groups being optionally substituted by halogen, —CN, —$NO_2$, aryl, heteroaryl, —$COR^6$, —$CO_2R^6$, —$CON(R^6)_2$, —$OCOR^7$, —$NR^6COR^7$, —$NR^6SO_2R^7$, —$SO_3R^6$, —$SO_2N(R^6)_2$, —$OR^6$, —$SR^6$ or —$N(R^6)_2$; or when X is N—$R^a$, $R^1$ together with $R^a$ completes a fused imidazole or 4,5-dihydroimidazole ring;

$R^2$ and $R^{2a}$ each represents hydrogen, or $R^2$ and $R^{2a}$ together complete a fused lactam ring of 4–7 members;

$R^3$ represents aryl, heteroaryl, $C_{1-6}$alkyl, polyfluoro$C_{1-6}$alkyl, $C_{3-8}$cycloalkyl or $C_{3-8}$cycloalkyl$_{1-6}$alkyl;

each $R^6$ independently represents H, polyfluoro$C_{1-6}$alkyl, or $C_{1-6}$alkyl which is optionally substituted with halogen, —CN, —$NO_2$, —OH, —SH, —$NH_2$, phenyl, $C_{1-4}$alkoxy, $C_{1-4}$alkylthio, $C_{1-4}$alkylamino, di($C_{1-4}$alkyl)amino, —$CO_2H$, —$CO_2C_{1-4}$alkyl, —$CONH_2$, —$CONHC_{1-4}$alkyl or —$CON(C_{1-4}$alkyl$)_2$; or two $R^6$ groups attached to a single nitrogen atom may complete a heterocyclic ring of from 3 to 12 members including the said nitrogen, the remaining atoms being selected from C, N, O and S, and the ring optionally bearing up to 3 substituents independently selected from $C_{1-6}$alkyl, polyfluoro$C_{1-6}$alkyl, $C_{2-7}$acyl, —OH and —$CONH_2$;

$R^7$ represents $R^6$ that is other than H;

"aryl" refers to phenyl which is optionally fused to a 5–7 membered saturated or unsaturated ring which may be carbocyclic or may comprise up to 3 heteroatoms selected from nitrogen, oxygen and sulphur, and which may be oxo-substituted, said phenyl and optional fused ring together bearing 0–3 substituents independently selected from $C_{1-6}$alkyl [which is optionally substituted with halogen, —CN, —NO$_2$, —OH, —SH, —NH$_2$, $C_{1-4}$alkoxy, $C_{1-4}$alkylthio, $C_{1-4}$alkylamino, di($C_{1-4}$alkyl)amino, —CO$_2$H, —CO$_2$C$_{1-4}$alkyl, —CONH$_2$, —CONHC$_{1-4}$alkyl or —CON(C$_{1-4}$alkyl)$_2$], polyfluoroC$_{1-6}$alkyl, halogen, —CN, —NO$_2$, heteroaryl, —COR$^6$, —CO$_2$R$^6$, —CON(R$^6$)$_2$, —OCOR$^7$, —NR$^6$COR$^7$, —NR$^6$SO$_2$R$^7$, —SO$_3$R$^6$, —SO$_2$N(R$^6$)$_2$, —OR$^6$, —SR$^6$ and —N(R$^6$)$_2$;

"heteroaryl" refers to a heteroaromatic ring of 5 or 6 members, at least one member being nitrogen, oxygen or sulphur and the remainder carbon, said zing optionally being fused to a 5–7 membered saturated or unsaturated ring which may be carbocyclic or may comprise up to 3 heteroatoms selected from nitrogen, oxygen and sulphur, and which may be oxo-substituted, the heteroaromatic ring and optional fused ring together bearing 0–3 substituents independently selected from $C_{1-6}$alkyl [which is optionally substituted with halogen, —CN, —NO$_2$, —OH, —SH, —NH$_2$, $C_{1-4}$alkoxy, $C_{1-4}$alkylthio, $C_{1-4}$alkylamino, di($C_{1-4}$alkyl)amino, —CO$_2$H, —CO$_2$C$_{1-4}$alkyl, —CONH$_2$, —CONHC$_{1-4}$ alkyl or —CON(C$_{1-4}$alkyl)$_2$], polyfluoroC$_{1-6}$alkyl, halogen, —CN, —NO$_2$, phenyl, —COR$^6$, —CO$_2$R$^6$, —CON(R$^6$)$_2$, —OCOR$^7$, —NR$^6$COR$^7$, —NR$^6$SO$_2$R$^7$, —SO$_3$R$^6$, —SO$_2$N(R$^6$)$_2$, —OR$^6$, —SR$^6$ and —N(R$^6$)$_2$;

or a pharmaceutically acceptable salt thereof

Where a variable occurs more than once in formula I or in a substituent thereof, the individual occurrences of that variable are independent of each other, unless otherwise specified.

As used herein, the expression "$C_{1-x}$alkyl" where x is an integer greater than 1 refers to straight-chained and branched alkyl groups wherein the number of constituent carbon atoms is in the range 1 to x. Particular alkyl groups are methyl, ethyl, n-propyl, isopropyl and t-butyl. Derived expressions such as "$C_{2-6}$alkenyl", "hydroxyC$_{1-6}$alkyl", "heteroarylC$_{1-6}$alkyl", "$C_{2-6}$alkynyl" and "$C_{1-6}$alkoxy" are to be construed in an analogous manner.

The expression "polyfluoroC$_{1-6}$alkyl" as used herein refers to alkyl groups as defined above comprising at least one —CF$_2$— and/or —CF$_3$ group.

The expression "$C_{2-7}$acyl" as used herein refers to aromatic or linear, branched or cyclic aliphatic keto groups of up to 7 carbon atoms including the carbonyl group. Halogenated derivatives are encompassed. Examples include acetyl, trifluoroacetyl, benzoyl, n-propanoyl, isopropanoyl and cyclopentanoyl.

As used herein, the expression "$C_{3-x}$cycloalkyl" where x is an integer greater than 3 refers to nonaromatic hydrocarbon ring systems comprising from 3 to x ring atoms. Where the specified number of ring atoms permits, the definition includes polycyclic systems, including spirocyclic ortho-fused (including benzo-fused, provided attachment of the cycloalkyl group is via the non-aromatic ring) and bridged bicyclic systems. "Spirocyclic" refers to a pair of rings having a single atom in common. "Ortho-fused" refers to a pair of rings having two adjacent atoms in common. "Bridged bicyclic" refers to a pair of rings having at least three adjacent atoms in common. Examples of cycloalkyl groups therefore include cyclopropyl, cyclobutyl, cyclopentyl, cyclohexyl, cyclohexenyl, indanyl, decalinyl, and bicyclo[2,2,1]hept-1-yl.

As used herein, the expression "heterocyclic ring" refers to monocyclic ring systems comprising ring atoms selected from carbon, oxygen, nitrogen and sulphur, at least one ring atom being other than carbon. Examples include azetidine, pyrrolidine, piperidine, piperazine, morpholine and thiomorpholine.

As used herein, the expression "aryl" refers to phenyl which is optionally fused to a 5–7 membered saturated or unsaturated ring which may be carbocyclic or may comprise up to 3 heteroatoms selected from nitrogen, oxygen and sulphur, and which may be oxo-substituted, said phenyl and optional fused ring together bearing 0–3 substituents as described previously. The definition thus includes substituted and unsubstituted phenyl and naphthyl groups, and also groups comprising a phenyl ring which is fused to a saturated or unsaturated carbocyclic or heterocyclic ring, provided attachment of the aryl group is via the phenyl ring. The fused ring may be oxo-substituted, and hence may be a cyclic lactone or lactam. Examples of aryl groups therefore also include methylenedioxyphenyl, quinolinyl, 1,2,3,4-tetrahydroquinolinyl, benzofuranyl, indolyl and 2-oxoisoindolyl.

As used herein, the expression "heteroaryl" refers to a heteroaromatic ring of 5 or 6 members, at least one member being nitrogen, oxygen or sulphur and the remainder carbon, said ring optionally being fused to a 5–7 membered saturated or unsaturated ring which may be carbocyclic or may comprise up to 3 heteroatoms selected from nitrogen, oxygen and sulphur, and which may be oxo-substituted, the heteroaromatic ring and optional fused ring together bearing 0–3 substituents as described previously. Generally, not more than 4, and preferably not more than 3 atoms of the heteroaromatic ring are other than carbon. Where a heteroaromatic ring comprises two or more atoms which are not carbon, not more than one of said atoms may be other than nitrogen. Examples of heteroaromatic rings include pyridine, pyridazine, pyrimidine, pyrazine, pyrrole, furan, thiophene, pyrazole, oxazole, isoxazole, thiazole, isothiazole, imidazole, oxadiazole, triazole, thiadiazole, tetrazole, 1,2,4-triazine and 1,3,5-triazine. The optional fused ring may be saturated or unsaturated, including rings which are themselves (hetero)aromatic. Thus, for example, benzo-fused derivatives of the above-listed heteroaromatic rings (where they are possible) are included within the definition, provided attachment of the heteroaryl group is via the heteroaromatic ring.

When a hydroxy substituent is present on a heteroaromatic ring and keto-enol tautomerism is possible, both tautomers are to be considered as falling within the scope of the invention.

The term "halogen" as used herein includes fluorine, chlorine, bromine and iodine.

For use in medicine, the compounds of formula I may advantageously be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention. However, the stereochemistry at the position marked with an asterisk (*) in formula I is preferably as shown in formula Ia:

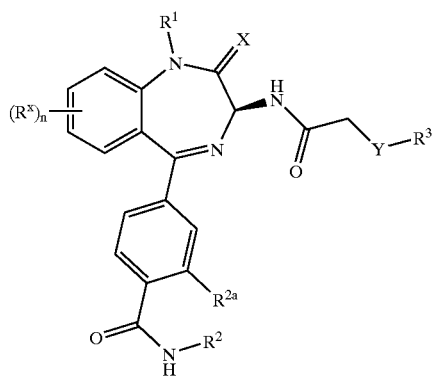

Ia

In the compounds of formula I, n is preferably 0–2, most preferably 0 or 1.

$R^x$ is preferably halogen or $C_{1-6}$alkyl, most preferably halogen, especially chlorine. When n is 1, the substituent $R^x$ is preferably in the 7-position (i.e. para with respect to the nitrogen atom bonded to $R^1$).

X represents O, S or N—$R^a$ where $R^a$ combines with $R^1$ to complete a fused imidazole or 4,5-dihydroimidazole ring. Typically X is O or N—$R^a$, and preferably X is O.

Y represents —CH$_2$—, —CH(OH)—, —CH(CH$_3$)—, —CH$_2$O—, —O— or —S—; preferably —CH$_2$—, —CH(OH)—, —CH(CH$_3$)—, —CH$_2$O— or —O—.

Typically, $R^1$ represents H, polyfluoroC$_{1-6}$alkyl or C$_{1-6}$alkyl which is optionally substituted with halogen, CN, aryl, heteroaryl, —CO$_2$R$^6$, —CON(R$^6$)$_2$, —OR$^6$ or —N(R$_6$)$_2$ where aryl, heteroaryl and R$^6$ are as defined above, or $R^1$ combines with X to complete a fused imidazole or 4,5-dihydroimidazole ring. Preferably, $R^1$ represents H, polyfluoroC$_{1-6}$alkyl or C$_{1-4}$alkyl which is optionally substituted with —CN, —OH, azyl, heteroaryl, —CONH$_2$, C$_{1-6}$alkoxy or —N(R$^{6a}$)$_2$ where each R$^{6a}$ independently represents H or C$_{1-6}$alkyl, or the two R$^{6a}$ groups together complete a pyrrolidinyl, piperidinyl, piperazinyl or morpholinyl ring, or $R^1$ combines with X to complete a fused imidazole or 4,5-dihydroimidazole ring. Specific embodiments of $R^1$ include H, methyl, isopropyl, 2,2,2-trifluoroethyl, 4-methoxybenzyl, 3-(morpholin-4-yl)propyl, 3-(pyrrolidin-1-yl)propyl, cyanomethyl, carbamoylmethyl, 5-chloro-1,2,3-thiadiazol-4-ylmethyl, 3-hydroxypropyl and 3-dimethylaminopropyl. Most preferably, $R^1$ represents methyl or 2,2,2-trifluoroethyl.

$R^2$ and $R^{2a}$ are either both hydrogen, or together complete a fused lactam ring of 4–7 members which may be fully saturated or may contain unsaturation. Preferably, a fused lactam ring completed by $R^2$ and $R^{2a}$ is 5- or 6-membered. In preferred embodiments, $R^2$ and $R^{2a}$ are either both hydrogen or together complete a fused pyrrolidinone or piperidinone ring.

$R^3$ may represent aryl, heteroalkyl, C$_{1-6}$alkyl, polyfluoroC$_{1-6}$alkyl, C$_{3-8}$-cycloalkyl or C$_{3-8}$cycloalkylC$_{1-6}$alkyl, but typically represents polyfluoroC$_{1-6}$alkyl (such as CF$_3$), aryl or heteroaryl. In particular, $R^3$ represents phenyl which optionally bears up to 3, but preferably not more than 2, substituents independently selected from C$_{1-4}$alkyl, C$_{1-4}$alkoxy, trifluoromethyl and halogen atoms. Preferred embodiments of $R^3$ include phenyl, methylphenyl, methoxyphenyl, bis(trifluoromethyl)phenyl, chlorophenyl, fluorophenyl, dichlorophenyl and difluorophenyl. Particularly preferred embodiments include 2,4-dichlorophenyl, 2,4-difluorophenyl, 3,4-dichlorophenyl and 3,4-difluorophenyl.

A subclass of the compounds of formula I is defined by formula II:

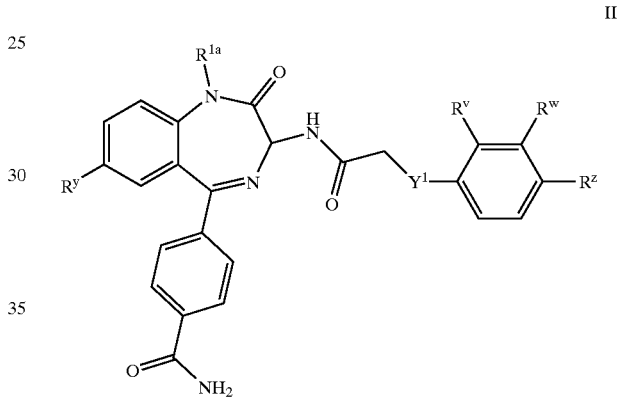

II wherein:
$R^y$, $R^z$, $R^v$ and $R^w$ are independently H or halogen;
$Y^1$ is —CH$_2$—, —CH(OH)—, —CH(CH$_3$)—, —CH$_2$O— or —O—; and
$R^{1a}$ is H, polyfluoroC$_{1-4}$alkyl, or C$_{1-4}$alkyl which is optionally substituted by —OH, —CN, carbamoyl or dimethylamino.

Another subclass of the compounds of formula I is defined by formula III:

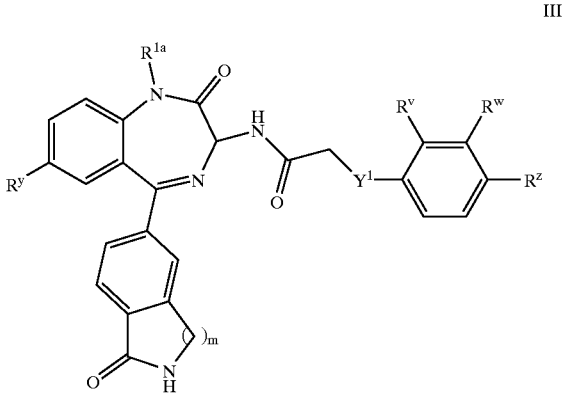

III wherein:

m is 1 or 2; and $R^y$, $R^z$, $R^v$, $R^w$, $Y^1$ and $R^{1a}$ are as defined above.

In the compounds of formulae II and III, preferably $R^z$ is halogen and one of $R^v$ and $R^w$ is H while the other is halogen. Most preferably, $R^z$ and $R^w$ are both chlorine or both fluorine and $R^v$ is H. $R^y$ is preferably H or chlorine, most preferably H.

Examples of compounds in accordance with the invention include those disclosed in the Examples appended hereto, and pharmaceutically acceptable salts thereof.

The invention also provides pharmaceutical compositions comprising one or more compounds of this invention and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums or surfactants such as sorbitan monooleate, polyethylene glycol, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly(vinylpyrrolidone) or gelatin.

The compounds of the invention are potent inhibitors of γ-secretase, with the ability to arrest the production of β-amyloid peptide, and hence are useful in the treatment or prevention of diseases involving the deposition of β-amyloid.

Therefore, in a further aspect of the invention, there is provided the use of a compound of formula I or a pharmaceutically acceptable salt thereof for the treatment or prevention of a condition associated with the deposition of β-amyloid.

Preferably, the condition is a neurological disorder having associated β-amyloid deposition, such as Alzheimer's disease.

The present invention further provides the use of a compound of formula I or a pharmaceutically acceptable salt thereof in the manufacture of a medicament for treating or preventing Alzheimer's disease.

Also disclosed is a method of treatment of a subject suffering from or prone to Alzheimer's disease which comprises administering to that subject an effective amount of a compound of formula I or a pharmaceutically acceptable salt thereof.

For treating or preventing Alzheimer's Disease, a suitable dosage level is about 0.01 to 250 mg/kg per day, preferably about 0.01 to 100 mg/kg per day, and especially about 0.01 to 5 mg/kg of body weight per day. The compounds may be administered on a regimen of 1 to 4 times per day. In some cases, however, dosage outside these limits may be used.

The compounds of formula I wherein X=O and $R^2=R^{2a}=H$ may be prepared by reaction of a compound of formula IV with a compound of Formula V:

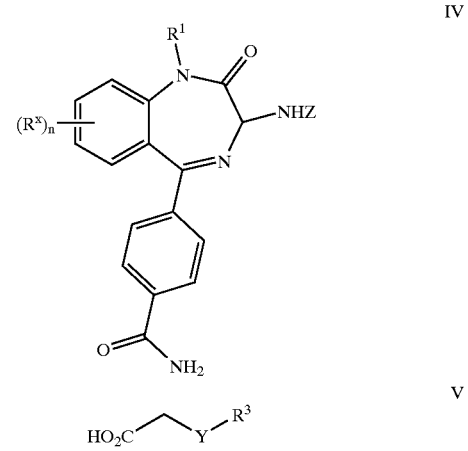

where Z represents a protecting group such as benzyloxycarbonyl, and $R^x$, n, $R^1$, $R^3$ and Y have the same meanings as before. The process involves removal of the protecting group Z by treatment with acid (e.g. a solution of HBr in acetic acid), followed by coupling of the resulting primary amine with carboxylic acid V. Any of the standard coupling methods may be used, such as treatment with 1-(3-dimethylaminopropyl)-3-ethylcarbodiimide hydrochloride (EDC), hydroxybenzotriazole hydrate (HOBt) and triethylamine in dichloromethane, or treatment with O-benzotriazol-1-yl-N,N,N',N'-tetramethyluronium hexafluorophosphate (HBTU) and triethylamine in acetonitrile.

The protected amine IV may be prepared by a process comprising reaction of the benzodiazepinedione VI with Grignard reagent VII to form adduct VIII:

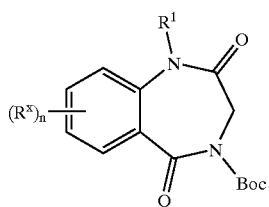

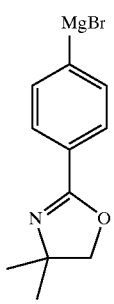

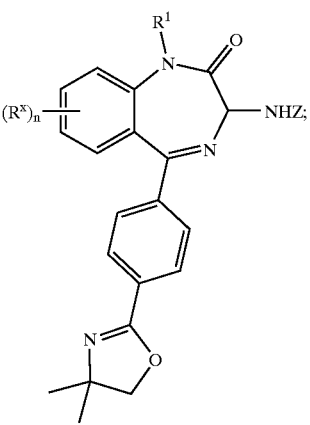

conversion of VIII to the protected amine IX:

conversion of the oxazolidine group of IX to carboxylic acid to form X:

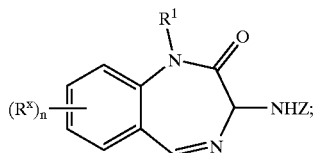

and conversion of the carboxylic acid group of X to carboxamide to form IV; wherein Boc represents t-butoxycarbonyl and Z, $R^x$, n and $R^1$ have the same meanings as before.

Diones of formula VI are available by the methods disclosed in WO97/49690, and Grignard reagent VII by the method described in *J. Org. Chem.*, 1974, 39, 2790. Adduct VIII is formed by reaction of VI with VII at −78° C. in THF, followed by treatment with HCl gas and saturated $NaHCO_3$ solution. Conversion VIII to the protected amine IX involves reaction of VIII with triisopropylbenzenesulfonyl azide in the presence of strong base (e.g. potassium hexamethyldisilazide) in THF at −78° C., followed by reduction of the resulting azide to the amine and addition of the protecting group Z. Any of the standard methods of reduction may be used, such as hydrogenation over a Pd/C catalyst. Conversion of the oxazolidine group to carboxylic acid may be achieved by sequential treatment of IX with dilute HCl, acetyl chloride and dilute NaOH. Finally, the conversion of the carboxylic acid group to carboxamide may be effected by conventional routes, e.g. treatment of X with ammonium chloride, EDC, HOBt and triethylamine in DMF solution.

An alternative process for the preparation of protected amines IV comprises reaction of a benzophenone XI with an N-protected benzotriazolylglycine XII to form the benzodiazepine derivative XIII:

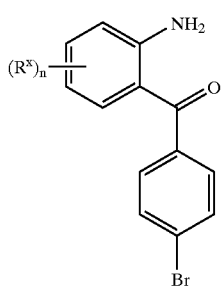

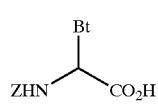

-continued

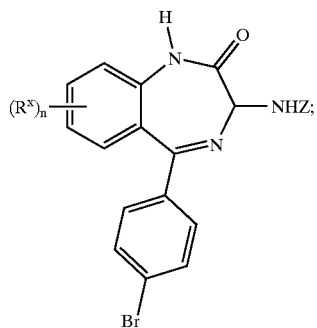
XIII optional N-alkylation of XIII to form the 1-substituted benzodiazepine XIV:

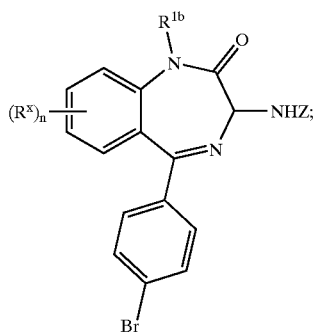
XIV and replacement of the bromine atom of XIII or XIV with a carbamoyl group to provide IV;

wherein Bt represents benzotriazol-1-yl, $R^{1b}$ represents $R^1$ that is other than H, and $R^x$, n and Z have the same meanings as before.

Benzophenones XI may be prepared as described in *J. Chem. Soc. Perkin Trans. I*, 1995, 203–212, and glycine derivative XII as described in *J. Org. Chem.* 55, 2206 (1990), while the reaction to form XIII may be carried out as described in *J. Org. Chem.* 60, 730–4 (1995). N-alkylation of XIII may carried out by conventional means, e.g. reaction with sodium hydride and $R^{1b}$-Hal in DMF, where Hal represents a leaving group such as halide, especially iodide, and $R^{1b}$ has the same meaning as before. Replacement of the bromine atom of XIV with a carbamoyl group may be achieved by reaction of XIV with carbon monoxide and hexamethyldisilazane in the presence of palladium (II) acetate, bis(diphenylphosphino)propane and a tertiary amine in DMF solution, followed by acid hydrolysis.

Compounds of formula I wherein X=O and $R^2$ and $R^{2a}$ complete a fused lactam zing may be prepared by reaction of the chlorides XV with the boronic acid derivatives XVI:

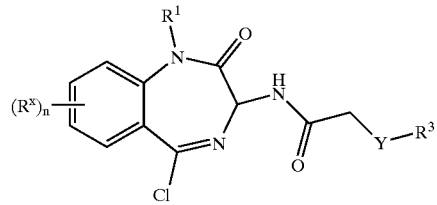
XV

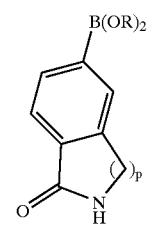
XVI where p is 0, 1, 2 or 3, each R is independently H or $C_{1-6}$alkyl or the two R groups together complete a borolane ring, and $R^x$, n, $R^1$, $R^3$ and Y have the same meanings as before. In particular, the R groups may individually represent H or together complete a 4,4,5,5-tetramethyl-1,3,2-dioxaborolane ring. The reaction takes place in the presence of a Pd(0) catalyst in DMF solution at elevated temperature in a sealed vessel.

The chlorides XV are available by a process comprising coupling of glycine derivative XII with aminobenzamide XVII to form amide XVIII:

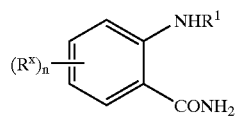
XVII

XVIII cyclisation of XVIII to form benzodiazepinedione XIX:

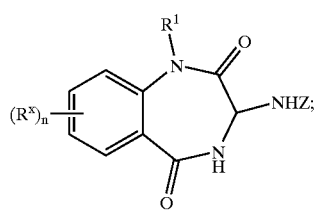
XIX coupling of XIX with carboxylic acid V to form amide XX:

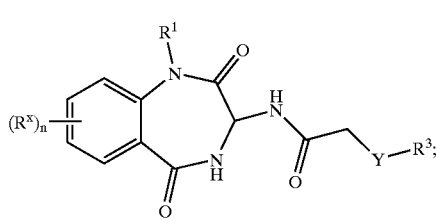
XX and treatment of XX with phosphoryl chloride to form chloride XV; where Z, Bt, R$^x$, n, R$^1$, R$^3$ and Y have the same meanings as before.

Coupling of XII with XVII is most readily achieved by conversion of the carboxylic acid group of XII to the acid chloride (e.g. by treatment with oxalyl chloride) prior to reaction with the amino group of XVII. Cyclisation of XVIII is effected by heating in DMSO at about 180° C. Coupling of XIX with V may be carried out under the same conditions as the reaction of IV with V. Conversion of XX to XV is effected by refluxing briefly (approx. 10 minutes) in phosphoryl chloride.

An alternative synthesis of the chlorides XV, particularly suitable for embodiments wherein R$^1$ represents H or polyfluoroalkyl, comprises ring-opening of isatoic anhydride XXI with 2,4,6-trimethoxybenzylamine to form amide XXII:

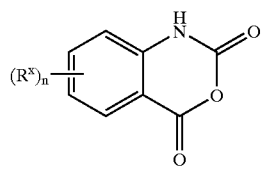
XXI

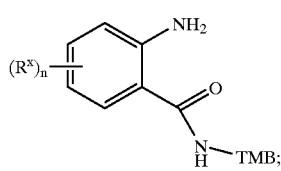
XXII reaction of XII with bromoacetyl bromide to form benzodiazepinedione XXIII:

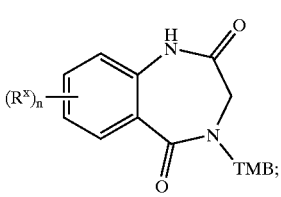
XXIII

N-alkylation of XXIII to provide XXIV:

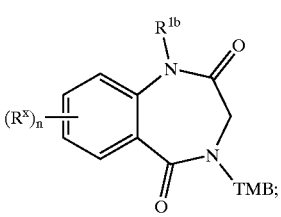
XXIV conversion of XXIV to the azide XXV and reduction thereof to the amine XXVI:

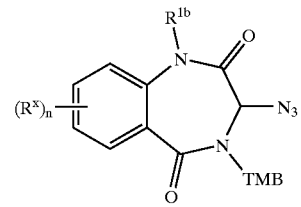
XXV

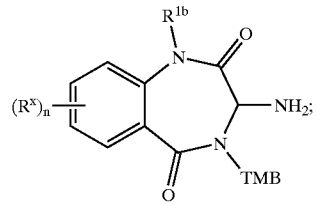
XXVI coupling of amine XXVI with carboxylic acid V followed by cleavage of the trimethoxybenzyl group to provide XX; and treatment of XX with phosphoryl chloride to provide chloride XV as described previously; where TMB represents 2,4,6-trimethoxybenzyl, and R$^x$, n and R$^{1b}$ have the same meanings as before.

Ring opening of XXI may be effected by refluxing with trimethoxybenzylamine in a solvent such as ethyl acetate in the presence of a tertiary amine. Cyclisation of XXI may be effected by treatment with bromoacetyl bromide at low temperature in the presence of alkali, and rafluxing of the resulting bromoacetalinide intermediate in sodium isopropoxide solution. N-alkylation of XXIII may be effected by any conventional means, but when R$^{1b}$ represents 2,2,2-trifluoroethyl, a particularly suitable process comprises treatment of XXII with 2,2,2-trifluoroethyl iodide and caesium carbonate in DMF at a temperature of about 55° C. Conversion of XXIV to the azide XXV may be carried out by treatment with potassium t-butoxide and 2,4,6-triisopropylbenzenesulfonyl azide in THF at −78° C., while reduction of the azide to provide amine XXVI is possible by of the conventional routes, notably treatment with triphenylphosphine in aqueous THF. Coupling of the amine XXVI with carboxylic acid V is possible by any of the conventional methods described previously, while cleavage of the TMB group involves treatment with a mixture of trifluoroacetic acid, water and dimethyl sulfide (approximately 90/5/5 by volume).

It will be appreciated that a given compound in accordance with formula I may be converted to another compound of formula I by the application of known synthetic techniques. For example, compounds of formula I in which X represents S may be prepared by treatment with Lawesson's reagent of the corresponding compounds in which X represents O. Alternatively, and advantageously, this reaction may be carried out on the synthetic precursors of such compounds, such as the compounds of formula IV. The reaction may be carried out as described in WO95/14693. The compounds of formula I, or the precursors thereof, wherein X represents N—R$^a$ may be prepared from the corresponding compounds in which X represents S using the methods disclosed in WO95/14693.

Similarly, a compound of formula I, or precursor thereof, in which R$^1$ represents hydroxyalkyl may be converted to the mesylate by reaction with methanesulfonyl chloride, and subjected to nucleophilic displacement with a primary or secondary amine to provide the corresponding aminoalkyl derivative.

The starting materials V, VI, VII, XI, XII, XVI, XVII and XXI, where they are not commercially available, may be prepared by standard procedures well known from the art, or by methods analogous to those described in detail hereinafter.

It will be appreciated that where more than one isomer can be obtained from a reaction then the resulting mixture of isomers can be separated by conventional means.

Where the above-described process for the preparation of the compounds according to the invention gives rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene. & P. G. M. Wuts, Protective Groups in Organic Synthesis, John Wiley & Sons, 1991. The protecting groups may be removed at a convenient subsequent stage using methods known from the art.

Assays which can be used to determine the level of activity of compounds of the present invention are disclosed in *Biochemistry*, 2000, 39(30), 8698–8704.

The Examples of the present invention all had an $ED_{50}$ of less than 10 μM, in preferred cases less than 1 μM, and in most preferred cases less than 100 nM in at least one of these assays.

EXAMPLES

The following schemes are representative of the methods used to prepare the compounds of the invention.

Procedures

Scheme 1

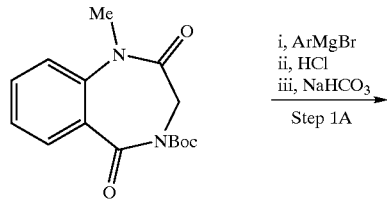

i, ArMgBr
ii, HCl
iii, NaHCO$_3$

Step 1A

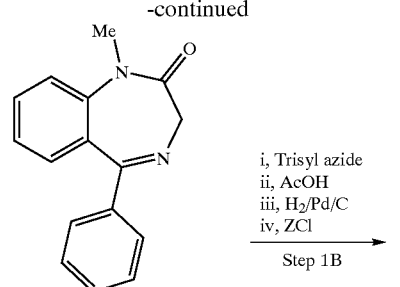

i, Trisyl azide
ii, AcOH
iii, H$_2$/Pd/C
iv, ZCl

Step 1B

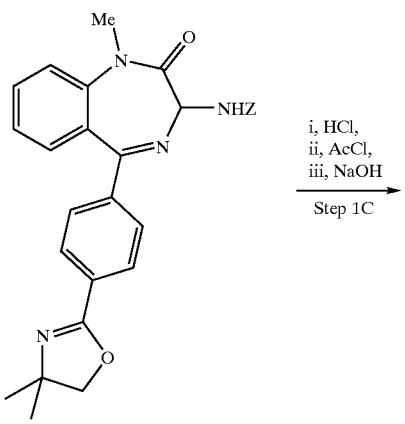

i, HCl,
ii, AcCl,
iii, NaOH

Step 1C

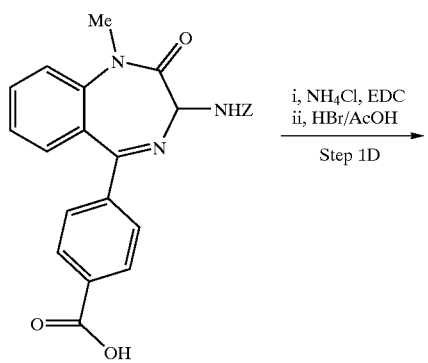

i, NH$_4$Cl, EDC
ii, HBr/AcOH

Step 1D

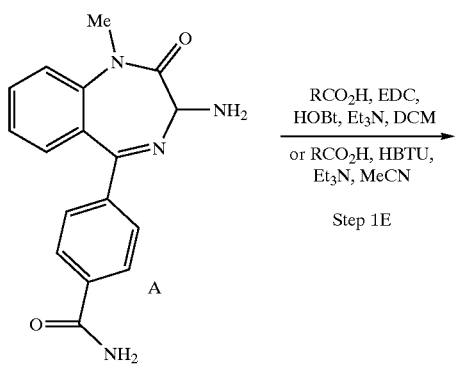

RCO$_2$H, EDC, HOBt, Et$_3$N, DCM
or RCO$_2$H, HBTU, Et$_3$N, MeCN

Step 1E

-continued

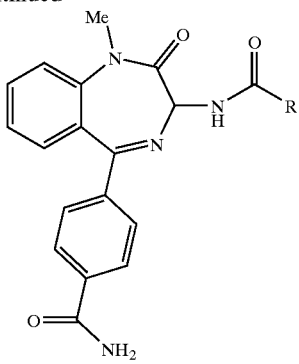

Scheme 1

Step 1A. To a stirred solution of 2-(4-bromophenyl)-4,4-dimethyl-4,5-dihydrooxazole (J. Org. Chem. 1974, 39, 2790) (9.15 g, 36.0 mmol.) in THF (100 ml) under nitrogen was added magnesium turnings (950 mg, 43.2 mmol.) and several crystals of iodine. The vigorously stirred mixture was gently warmed until the reaction had initiated. The mixture was allowed to self-reflux for 20 minutes and stirred a further 1 hour at room temperature. The resulting deep brown solution was added via cannula to a −78° C. solution of tert-butyl 1-methyl-2,5-dioxo-1,2,3,5-tetrahydro-4H-1,4-benzodiazepine-4-carboxylate (WO 97/49690) (9.50 g, 32.8 mmol.) in THF (100 ml) and stirred at −78° C. for 20 minutes. The cooling bath was removed and the reaction stirred for a further 2 hours after which time a saturated solution of NH$_4$Cl (100 ml) was added. The mixture was extracted into ethyl acetate (2×150 ml) and the combined organics dried (MgSO$_4$), evaporated and purified by column chromatography (SiO$_2$; ether) to afford the adduct 12.05 g, (79%) as an off-white solid. ($^1$H, CDCl$_3$) [exists as a ca. 4:1 mixture of rotamers—data for major rotamer only reported] 8.03 (2H, d, J=7 Hz), 7.79 (2H, d, J=8.5 Hz), 7.62 (1H, m), 7.47 (1H, m), 7.36 (1H, d, J=8 Hz), 5.36 (1H, br s), 4.14 (2H, s), 3.81 (1H, dd, J=18, 6 Hz), 3.60 (1H, dd, J=18 Hz), 3.08 (3H, s,) 1.40 (9H, s) and 1.39 (6H, s).

Into a stirred solution of the Boc-protected amine (12.0 g, 26 mmol.) in ethyl acetate (600 ml) cooled to −5° C. was bubbled HCl gas for 2.5 hours. After this time the solvent was evaporated to give a solid which was redissolved in a mixture of THF (200 ml) and saturated aqueous NaHCO$_3$ (300 ml). The mixture was vigorously stirred for 1 hour and extracted into ethyl acetate (2×300 ml). Drying (MgSO$_4$) and evaporation afforded the product as a solid (8.9 g, 99%). ($^1$H, CDCl$_3$) 7.96 (2H, d, J=8 Hz), 7.65 (2H, d, J=8 Hz), 7.56 (1H, t, J=8 Hz), 7.36 (1H, d, J=8 Hz), 7.25 (1H, d, J=8 Hz), 7.18 (1H, t, J=8 Hz), 4.83 (1H, d, J=10.5 Hz), 4.13 (2H, s), 3.79 (1H, d, J=10.5 Hz), 3.43 (3H, s) and 1.40 (6H, s).

Step 1B. To a stirred solution of benzodiazepinone (10.6 g, 30 mmol.) in THF (300 ml) at −78° C. was added potassium hexamethyldisilazide (0.5M solution in toluene, 86 ml, 43 mmol.) portionwise over 15 minutes and the mixture stirred for 10 minutes at −78° C. After this time, 2,4,6-triisopropylbenzenesulfonyl azide (10.86 g, 35 mmol.) as a solution in THF (75 ml) was added via cannula and the reaction stirred a further 10 minutes. A mixture of acetic acid (4 ml) and THF (75 ml) was then added, the cooling bath removed and the mixture stirred for 90 minutes. Saturated NaHCO$_3$ solution (200 ml) was added and the mixture extracted into ethyl acetate (3×150 ml). The combined organics were dried (MgSO$_4$) and evaporated to give a solid which was triturated with ether to afford the desired azide as a colourless solid (9.1 g, 77%). ($^1$H, CDCl$_3$) 7.99 (2H, d, J=8.5 Hz), 7.72 (2H, d, J=8.5 Hz), 7.62 (1H, t, J=8 Hz), 7.40 (1H, d, J=8 Hz), 7.32 (1H, d, J=8 Hz), 7.25 (1H, t, J=8 Hz), 4.56 (1H, s), 4.14 (2H, s), 3.49 (3H, s) and 1.40 (6H, s).

A solution of the azide (5.95 g, 15 mmol.) in ethanol (150 ml) was degassed with nitrogen bubbling for 10 minutes and then 5% palladium on charcoal (100 mg) added and the mixture hydrogenated at 35 psi H$_2$ for 60 minutes. The mixture was filtered through a pad of Celite washing well with ethanol and the combined organics evaporated to afford the amine (5.5 g 99%). ($^1$H, CDCl$_3$) 7.96 (2H, d, J=8 Hz), 7.66 (2H, d, J=8 Hz), 7.58 (1H, t, J=8 Hz), 7.37 (1H, d, J=8 Hz), 7.27 (1H, d, J=8 Hz), 7.20 (1H, t, J=8 Hz), 4.49 (1H, s), 4.13 (2H, s), 3.48 (3H, s) and 1.40 (6H, s).

To a stirred solution of the amine (5.6 g, 15.4 mmol.) and sodium carbonate (1.97 g, 18.6 mmol.) in a mixture of dioxan (200 ml) and water (100 ml) at 0° C. was added benzyl chloroformate (2.4 ml, 16.8 mmol.) dropwise. The mixture was stirred for 75 minutes at 0° C., quenched with saturated ammonium chloride solution (200 ml) and extracted into ethyl acetate (2×200 ml). The combined organics were dried (MgSO$_4$) and evaporated to afford the product as a foam (7.7 g, 99%). (1H, CDCl$_3$) 7.95 (2H, d, J=8 Hz), 7.65–7.59 (3H, m), 7.39–7.23 (8H, m), 6.72 (1H, d, J=8 Hz), 5.32 (1H, d, J=8 Hz), 5.15 (2H, ABq), 4.14 (2H, s), 3.48 (3H, s) and 1.40 (6H, s).

Step 1C. The oxazoline (7.7 g, 15.5 mmol.) was dissolved in a mixture of dioxan (50 ml) and 1M HCl (150 ml) and stirred at ambient temperature for 24 h. After this time, the mixture was cautiously basified with sodium carbonate solution and extracted into ethyl acetate (3×150 ml) and dichloromethane (2×100 ml). The combined organic extracts were dried (MgSO$_4$), evaporated and then redissolved in dichloromethane (100 ml). The solution was cooled to 0° C., triethylamine (1.4 ml, 10 mmol.) and acetyl chloride (0.66 ml, 9.2 mmol.) added and the mixture stirred at ambient temperature for 1 hour. The solvent was evaporated and the residue taken up in a mixture of THF (100 ml) and 1N NaOH (30 ml) and the mixture stirred for a further 18 hours. After this time, the solution was washed with ether (100 ml) and the aqueous layer acidified to pH 2 with 1N HCl and extracted into ethyl acetate (3×100 ml). The combined ethyl acetate layers were dried (MgSO$_4$) and evaporated to afford the product as an oil (3.5 g, 51%). ($^1$H, CDCl$_3$) 8.09 (2H, d, J=8.5 Hz) 7.75–7.59 (4H, m), 7.41–7.24 (7H, m), 6.74 (1H, d, J=8 Hz), 5.34 (1H, d, J=8 Hz), 5.15 (2H, ABq) and 3.48 (3H, s).

Step 1D. To a stirred solution of carboxylic acid (4.25 g, 9.6 mmol.) in DMF (75 ml) was added ammonium chloride (5.0 g, 95 mmol.), EDC (2.21 g, 11.5 mmol.), HOBt (1.56 g, 11.5 mmol.) and triethylamine (20 ml) and the Mixture stirred at ambient temperature for 18 h. The solvent was evaporated and the residue taken up in ethyl acetate (100 ml), washed with 1N HCl (100 ml), saturated NaHCO$_3$ solution (100 ml) and water (3×100 ml). The organic layer was dried (MgSO$_4$) and evaporated to give a yellow powder which was triturated with ether to afford an off-white powder (2.7 g, 64%). ($^1$H, CDCl$_3$) 7.82 (2H, d, J=8.5 Hz), 7.75–7.59 (4H, m), 7.41–7.23 (7H, m) 6.72 (1H, d, J=8 Hz), 6.1 (1H, br s), 5.65 (1H, br, s), 5.33 (1H, d, J=8 Hz), 5.15 (2H, ABq) and 3.48 (3H, s).

To this benzyl carbamate (1.45 g, 3.3 mmol.) was added HBr (45% in acetic acid, 9 ml) and the mixture stirred at ambient temperature until all the starting material had dissolved (35 minutes). The resulting bright orange solution was poured into ice cold ether (150 ml) and vigorously stirred for 10 minutes at 0° C. and filtered. The resulting pale yellow solid was partitioned between 4N NaOH (75 ml) and dichloromethane (100 ml), the layers separated and the aqueous layer extracted with further dichloromethane (3×100 ml) and 10% v/v methanol/dichloromethane (2×100 ml). The combined organic layers were dried (MgSO$_4$) and evaporated to give a yellow semi-solid which was triturated with ether to afford the product as an off-white powder (850

(ii), To a stirred solution of benzodiazepine amine (0.3 mmol.) in acetonitrile (5 ml) under nitrogen was added the carboxylic acid (0.33 mmol.), HBTU (0.33 mmol.) and triethylamine (0.6 mmol.) and the mixture stirred at ambient temperature for 12–24 h. The mixture was lyophilized and the residue purified by HPLC using an appropriate eluent.

The product from Step 1D (designated A) could alternatively be prepared by the route shown in Scheme 2.

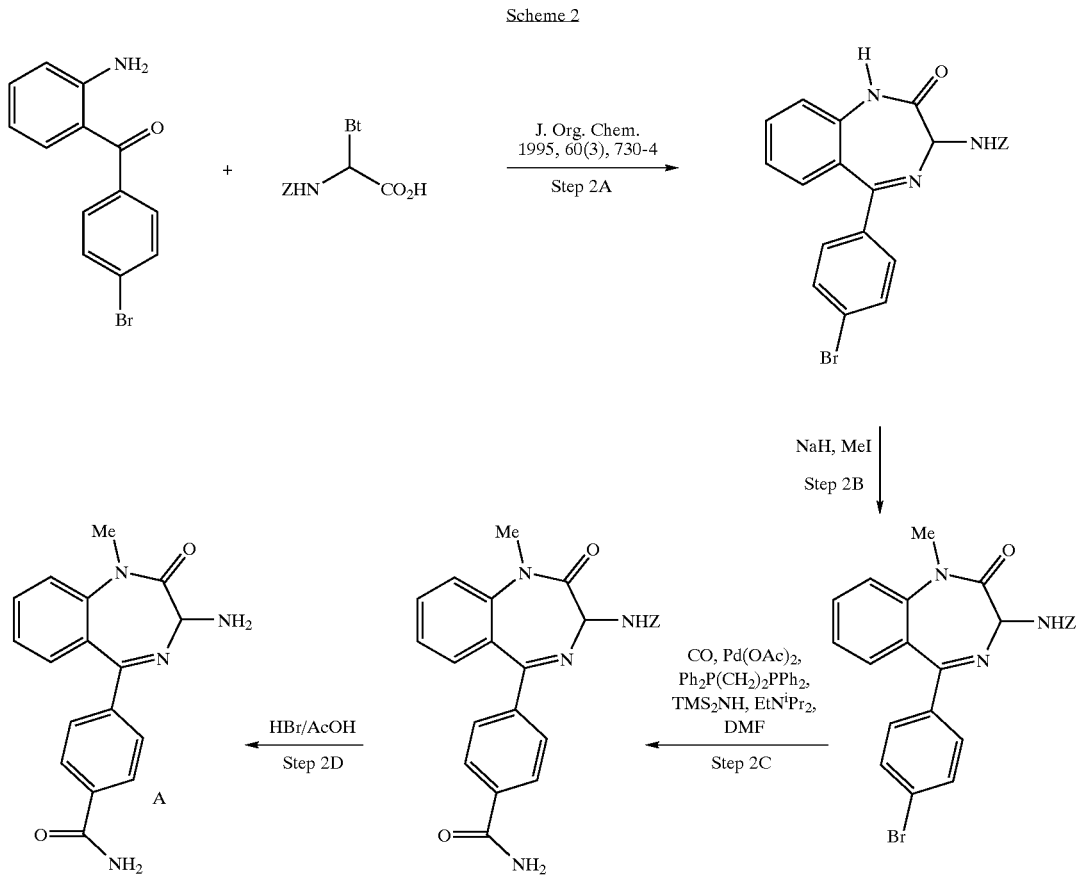

Scheme 2 mg, 84%). ($^1$H, CDCl$_3$) 7.83 (2H, d, J=8 Hz), 7.72 (2H, d, J=8 Hz), 7.60 (1H, t, J=8 Hz), 7.38 (1H, d, J=8 Hz), 7.28 (1H, d, J=8 Hz), 7.22 (1H, t, J=8 Hz), 6.72 (1H, d, J=8 Hz), 6.15 (1H, br s), 5.65 (1H, br s), 4.49 (1H, s) and 3.48 (3H, s).

Step 1E Representative Procedures.

(i), To a stirred solution of benzodiazepine amine (0.3 mmol.) in dichloromethane or DMF (5 ml) under nitrogen was added the carboxylic acid (0.33 mmol.), EDC (0.33 mmol.), HOBt (0.33 mmol.) and triethylamine (0.6 mmol.) and the mixture stirred at ambient temperature for 12–24 h. The mixture was diluted with further dichloromethane (25 ml), washed successively with 1N HCl (25 ml) [this washing omitted for products bearing basic centres], 1N NaOOH (25 ml) and brine, dried (MgSO$_4$) and evaporated. The residue was purified by HPLC, column chromatography or preparative thin layer chromatography on silica using an appropriate eluent.

Scheme 2

Step 2A. [5-(4-bromophenyl)-2-oxo-2,3-dihydro-1H-benzo[e][1,4]-diazepin-3-yl]-carbamic acid benzyl ester.

2-Amino-4'-bromobenzophenone (*J. Chem. Soc, Perkin Trans.* 1, 1995, 203–212) and the 2-(benzotriazol-1-yl)-N-(benzyloxycarbonyl)glycine (A. R. Katritzky et al, *J. Org. Chem.*, 1990, 55, 2206) were reacted in an analagous fashion to that described in *J. Org. Chem.* 1995, 60, 730–4 to give the title compound. $^1$H-NMR (DMSO) 5.02–5.07 (3H, m), 7.25–7.67 (14H, m), 8.45 (1H, d).

Step 2B. [5-(4-bromophenyl)-1-methyl-2-oxo-2,3-dihydro-1H-benzo[e][1,4]-diazepin-3-yl]-carbamic acid benzyl ester.

The product from Step 2A (8 g, 0.0172 moles) was dissolved in DMF (120 ml) and treated with a 60% dispersion of sodium hydride in mineral oil (760 mg, 0.019 moles) followed by iodomethane (2.94 g, 0.021 moles) and allowed to stir at ambient temperature for 16 hours. The reaction was quenched with water (100 ml) and extracted into ethyl acetate (2×100 ml). The combined organic layers were washed with water (100 ml) and brine (100 ml), dried (MgSO$_4$) and evaporated in vacuo. Purification by chromatography (SiO$_2$, 1% diethylether/dichloromethane) followed by trituration with ether afforded the title compound (3.5 g, 43%). $^1$H NMR (DMSO) 3.38 (3H, s), 5.06 (2H, s), 5.09 (1H, d, J=8.5 Hz), 7.34–7.68 (13H, m), 8.50 (1H, d).

Step 2C. [5-(4-carbamoyl-phenyl)-1-methyl-2-oxo-2,3-dihydro-1H-benzo[e][1,4]diazepin-3-yl]-carbamic acid benzyl ester.

A solution of the product from Step 2B (3.5 g, 0.0073 moles), 1,3-bis(diphenylphosphino)propane (305 mg, 0.00073 moles), hexamethyldisilane (10.8 ml, 0.0146 moles), and N,N-diisopropylethylamine (2.5 ml, 0.0146) in DMF were degassed with nitrogen bubbling for ten minutes. Palladium (II) acetate (162 mg, 0.00073 moles) was added and the mixture degassed for a further five minutes. Carbon monoxide gas was bubbled through the reaction mixture for 5 minutes at room temperature and then for 6 hours at 1100° C. After this time, the reaction mixture was cooled and partitioned between dichloromethane (50 ml) and water (50 ml). The aqueous layer was extracted with further dichloromethane (3×50 ml) and the combined organic layers washed with water (100 ml) and brine (100 ml), dried (MgSO$_4$) and evaporated in vacuo. The residue was taken up in a mixture of THF (150 ml) and 2M HCl (30 ml) and stirred at ambient temperature for one hour. The THF was then evaporated in vacuo and the residue partitioned between dichloromethane (50 ml) and 2M NaOH (50 ml). The aqueous layer was extracted with dichloromethane (2×50 ml) and the combined organic layers washed (H$_2$O, brine), dried (MgSO$_4$) and evaporated in vacuo. Purification by chromatography (SiO$_2$, 1% MeOH/CHCl$_3$) gave the title compound. $^1$H NMR (DMSO) 3.31 (3H, s), 5.07 (2H, s), 5.12 (1H, d), 7.30–7.80 (12H, m), 7.93 (2H, d, J=8.4 Hz), 8.08 (1H, br s), 8.50 (1H, d). MS (ES+) MH$^+$=443

Step 2D. 4-(3-amino-1-methyl-2-oxo-2,3-dihydro-1H-benzo[e][1,4]diazepin-5-yl)-benzamide.

To the product from Step 2C (400 mg, 0.9 mmol.) was added hydrogen bromide (45 wt % in acetic acid, 2 ml) and the mixture stirred until dissolution was complete (30 minutes). After this time, the orange solution was poured into ice cold ether (20 ml) and vigorously stirred for 10 minutes. The resulting precipitate was filtered and washed with cold ether to give the title compound (220 mg, 80%).

$^1$H NMR (CDCl$_3$) 3.08 (3H, s), 4.50 (1H, s), 5.70 (1H, v br s), 6.15 (1H, v br s) 7.20–7.42 (5H, m), 7.57–7.85 (5H, m). MS (ES+) MH$^+$=309.

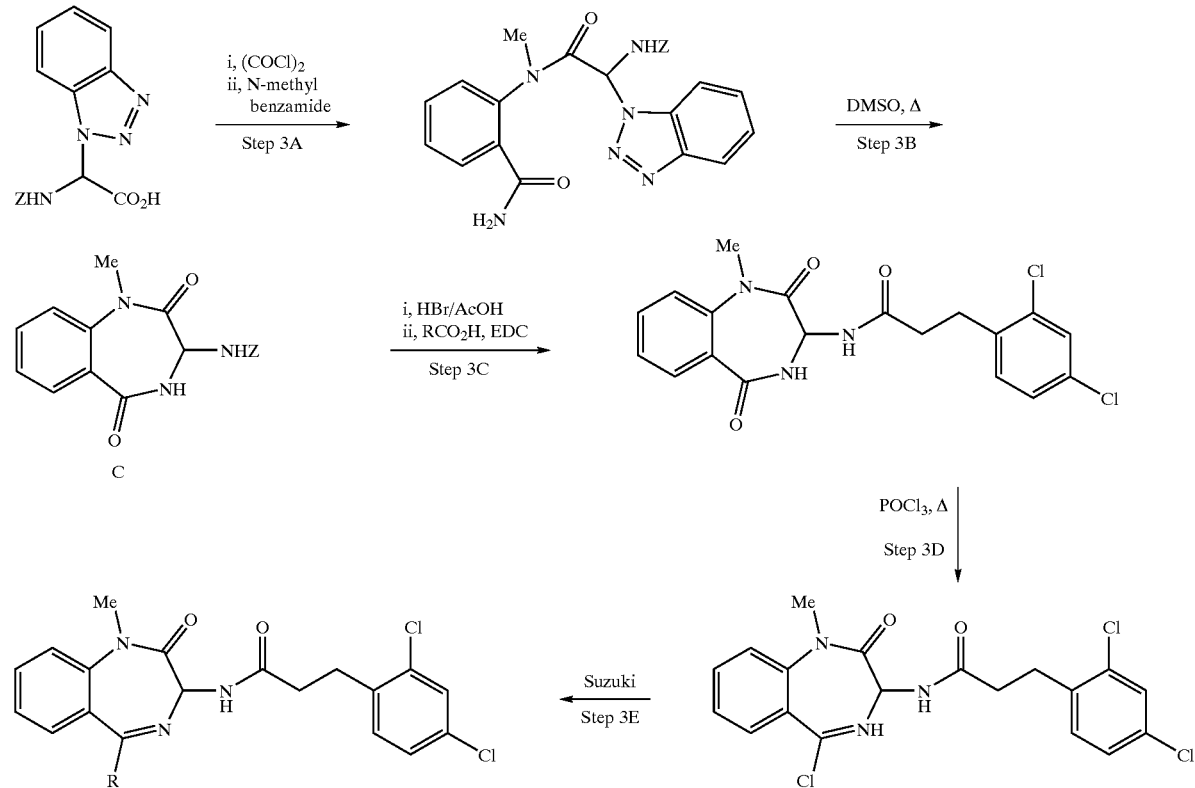

Scheme 3

Step 3A. Benzotriazol-2-yl-[(2-carbamoyl-phenyl)-methyl-carbamoyl]-methyl}-carbamic acid benzyl ester A solution of 2-benzotriazol-1-yl)-N-(benzyloxycarbonyl)glycine (A. R. Katritzky et al, J. Org. Chem., 1990, 55, 2206) (50 g, 0.15 mol) in THF (300 ml) at 0 C was treated slowly with oxalyl chloride (2.0 M in CH$_2$Cl$_2$, 81 ml, 0.16 mol) and DMF (1 ml). The reaction mixture was stirred at 0 C for 2 h, then treated with a solution of 2-(methylamino) benzamide (23 g, 0.15 mol) and 4-methylmorpholine (38 ml, 0.35 mol) in THF (100 ml). The reaction mixture was stirred overnight at 40 C, then filtered. The residue was partitioned between water and warm ethyl acetate. The aqueous layer was extracted three times with ethyl acetate. The combined extracts were combined with the original filtrate, dried (MgSO$_4$), filtered and evaporated in vacuo. Trituration with ethyl acetate gave the product as a white powder (23 g, 33%). The mother liquors were evaporated and purified by column chromatography to give a further quantity of the product (21 g, 30%). ($^1$H NMR, DMSO) 9.3 (1H, d), 8.8 (1H, d), 8.15–6.90 (15H, m), 4.92–4.75 (2H, m), 3.12 (3H, d, J=4.2 Hz).

Step 3B. (1-Methyl-2,5-dioxo-2,3,4,5-tetrahydro-1H-benzo[e][1,4]diazepin-3-yl)-carbamic acid benzyl ester The product from Step 3A (23 g, 0.05 mol) was added to DMSO (500 ml) at 180 C. The reaction mixture was stirred at 180 C for 20 min, cooled and diluted with 1 M NaOH (aq) and ether. The aqueous phase was extracted with ethyl acetate (five times) and the combined organic phases were washed with brine, dried, filtered and evaporated. Purification by column chromatography gave the product (5.8 g, 34%) as a yellow solid. ($^1$, HMR, DMSO) 9.30 (1H, d, J=4.0 Hz), 9.0 (3H, br s), 7.75–7.68 (2H, m), 7.56 (1H, d, J=8.1 Hz), 7.45–7.41 (1H, m), 5.20 (1H, d, J=4.2 Hz), 3.4 (3H, s).

Step 3C. 3-(3,4Dichloro-phenyl)-N-(1-methyl-2,5-dioxo-2,3,4,5-tetrahydro-1H-benzo[e][1,4]diazepin-3-yl)-propionamide.

The product from Step 3B (3.27 g, 9.64 mmol) was dissolved in 48% HBr—AcOH and stirred for 35 min. The reaction mixture was poured into a large volume of ice-cold ether. The resulting precipitate was collected by filtration, washed with ether and dried in vacuo. The product was obtained as a white solid (2.65 g, 96%). ($^1$H NMR, DMSO) 8.73 (1H, br d, J=3.6 Hz), 7.74–7.32 (10H, m), 5.21 (1H, dd, J=4.6, 7.8 Hz), 5.06 (2H, s), 3.31 (3H, s). MH+=340, MNa+=352.

This product was coupled to 3-(3,4-dichlorophenyl)propionic acid under standard conditions to yield the desired product. 1H NMR (DMSO) 8.73 (1H, d), 8.58 (1H, d) 7.74–7.31 (7H, m). 5.37 (1H, dd), 3.336 (3H, s) 2.93–2.82 (2H, m), 2.65–2.51 (2H, m). m/z=407 (C$_{19}$H$_{17}$N$_3$Cl$_2$O$_3$+H$^+$).

Step 3D. N-(5-Chloro-1-methyl-2-oxo-2,3-dihydro-1H-benzo[e][1,4]diazepin-3-yl)-3-(2,4-dichloro-phenyl)-propionamide.

The product from step 3C (1 g, 2.46 mmol) was finely ground, suspended in POCl$_3$ (ca 20 ml) and placed in an oil bath at 95 C. After approximately 10 minutes, the reaction mixture was cooled, diluted with ethyl acetate and added slowly to an ice-cold solution of NaHCO$_3$ containing ice. The mixture was shaken vigorously. The aqueous layer was separated and the organic layer was washed thoroughly with NaHCO$_3$ (twice), brine, dried (MgSO$_4$), filtered and evaporated in vacuo to give an orange solid. Trituration with ether gave the imidoyl chloride (0.7 g, 67%). $^1$H NMR (DMSO) 9.24 (1H, d, J=8.1), 7.87–7.74 (2H, m), 7.62–7.55 (2H, m), 7.48–7.33 (3H, m), 5.24 (1H, d, J 8.1), 3.37 (3H, s), 2.90–2.86 (2H, m), 2.61–2.55 (2H, m). m/z=424–428 (cluster) (C$_{19}$H$_{16}$N$_3$Cl$_3$O$_2$+H$^+$).

Step 3E Representative Procedure

The product from step 3D (100 mg, 0.23 mmoles), tripotassium phosphate (84 mg, 0.4 mmoles), 2-(1-oxo-2,3-dihydro-1H-isoindol-5-yl)-4,4,5,5-tetramethyl-1,3,2-dioxaborolane (91 mg, 0.35 mmoles) and DMF (4 ml) in a thick-walled flask were degassed with nitrogen. Pd(PPh$_3$)$_4$ was added and the vessel sealed and heated at 90° C. for 2 hours. The mixture was cooled and taken up in water/ethyl acetate. The organic layer was washed (water, brine), dried (MgSO$_4$) and evaporated in vacuo. Purification by flash silica column eluting with ethyl acetate gave the title compound.

Abbreviations:

EDC—1-(3-Dimethylaminopropyl)-3-ethylcarbodiimide hydrochloride

HOBt—Hydroxybenzotriazole hydrate

HBTU—O-Benzotriazol-1-yl)-N,N,N',N'-tetramethyluronium hexafluorophosphate

Example 1

(±)-4-[3-{[3-(2,4-dichlorophenyl)propanoyl]amino}-1-(3-[morpholin-4-yl]propyl)-2-oxo-2,3-dihydro-1H-1,4-benzodiazepin-5-yl]benzamide Prepared by modification of the route shown in Scheme 1. The starting material for Step 1A was tert-butyl 1-(3-(tert-butyldiphenylsilyloxy)propyl)-2,5-dioxo-1,2,3,5-tetrahydro-4H-1,4-benzodiazepine-4-carboxylate (prepared by analogy to WO 97/49690). During Step 1C, the silyl protecting group was cleaved and the resulting primary hydroxyl transformed to the morpholin-1-yl function by way of the mesylate using standard methods. Step 1E was carried out using 3-(2,4-dichlorophenyl)propionic acid.

($^1$H, CDCl$_3$) 1.64 (1H, m), 1.69 (1H, m), 2.15 (4H, m), 2.26 (2H, m), 2.70 (2H, m), 3.09 (2H, dd, J=6.8, 6.8), 3.60 (4H, m), 3.79 (1H, m), 4.40 (1H, m), 5.51 (2H, d, J=7.2), 5.82 (1H, brs), 6.21 (1H, brs), 7.17 (1H, m) 7.27 (3H, m), 7.38 (2H, m), 7.47 (1H, m), 7.61 (1H, m), 7.66 (2H, d, J=7.5), 7.83 (2H, d, J=7.5). MS(CI+): MH+=622

Example 2

(±)-4-[3-{[3-(2,4-dichlorophenyl)propanoyl]amino}-2-oxo-1-(3-[pyrrolidin-1-yl]propyl)-2,3-dihydro-1H-1,4-benzodiazepin-5-yl]benzamide hydrochloride Prepared by modification of the route shown in Scheme 1. The starting material for Step 1A was tert-butyl 1-(3-(tert-butyldiphenylsilyloxy)-propyl)-2,5-dioxo-1,2,3,5-tetrahydro-4H-1,4-benzodiazepine-4-carboxylate (prepared by analogy to WO 97/49690). During Step 1C, the silyl protecting group was cleaved and the resulting primary hydroxyl transformed to the pyrrolidin-1-yl-function by way of the mesylate using standard methods. Step 1E was carried out using 3-(2,4-dichlorophenyl)propionic acid.

(1H, DMSO) 1.82 (4H, m), 2.62–2.79 (4H, m), 2.90 (2H, m), 3.24 (1H, m), 3.36 (1H, m), 3.59 (4H, m), 3.91 (1H, m), 4.23 (1H, m), 5.32 (1H, d, J=7.8), 7.37 (4H, m), 7.49 (1H, brs), 7.58 (1H, d, J=1.9), 7.66 (2H, d, J=8.2), 7.76 (2H, d, J=3.6), 7.96 (2H, d, J=8.2), 8.11 (1H, brs), 9.23 (1H, d, J=7.8), 10.31 (1H, brs). MS(CI+): MH+=606

Example 3

(±)-4-[3-{[3-(2,4-dichlorophenyl)propanoyl]amino}-1-[3-(dimethylamino)propyl]-2-oxo-2,3-dihydro-1H-1,4-benzodiazepin-5-yl]benzamide hydrochloride Prepared by modification of the route shown in Scheme 1. The starting material for Step 1A was tert-butyl 1-(3-(tert-butyldiphenylsilyloxy)-propyl)-2,5-dioxo-1,2,3,5-tetrahydro-4H-1,4-benzodiazepine-4-carboxylate (prepared by analogy to WO 97/49690). During Step 1C, the silyl protecting group was cleaved and the resulting primary hydroxyl transformed to the dimethylamino function by way of the mesylate using standard methods. Step 1E was carried out using 3-(2,4-dichlorophenyl)-propionic acid.

(1H, DMSO) 1.88 (2H, m), 2.55 (3H, d, J=4.2), 2.59 (3H, d, J=4.2), 2.64 (2H, m), 2.82 (1H, m), 2.92 (3H, m), 3.89 (1H, m), 4.22 (1H, m), 5.33 (1H, d, J=7.7), 7.13 (1H, m), 7.24 (1H, m), 7.32 (2H, m), 7.37 (2H, m), 7.51 (1H, d, J=7.7), 10.35 (1H, brs). MS(CI+): MH+=580

Example 4

(±)-4-[3-{[3-(2,4-dichlorophenyl)propanoyl]amino}-1-(4-methoxybenzyl)-2-oxo-2,3-dihydro-1H-1,4-benzodiazepin-5-yl]benzamide Prepared by modification of the route shown in Scheme 1. The starting material for Step 1A was tert-butyl 1-(4-methoxybenzyl)-propyl)-2,5-dioxo-1,2,3,5-tetrahydro-4H-1,4-benzodiazepine-4-carboxylate (prepared by analogy to WO 97/49690) and Step 1E was carried out using 3-(2,4-dichlorophenyl)-propionic acid.

($^1$H, CDCl$_3$) 2.71 (2H, m), 3.11 (2H, m), 3.69 (3H, s), 4.69 (1H, d, J=14.9 Hz), 5.59 (1H, d, J=14.9 Hz), 5.59 (1H, d, J=8.0 Hz), 5.65 (1H, broad s), 6.12 (1H, broad s), 6.61 (2H, d, J=8.7 Hz), 6.89 (2H, d, J=8.7 Hz), 7.13–7.25 (4H, m), 7.34–7.40 (4H, m), 7.46–7.56 (2H, m), 7.76 (2H, d, J=8.4 Hz); MS(ES+), MH$^+$:615

Example 5

(±)-4-(3-{[3-(2,4-dichlorophenyl)propanoyl]amino}-2-oxo-2,3-dihydro-1H-1,4-benzodiazepin-5-yl)benzamide Prepared by modification of the route shown in Scheme 1. The starting material for Step 1A was tert-butyl 1-(4-methoxybenzyl)-propyl)-2,5-dioxo-1,2,3,5-tetrahydro-4H-1,4-benzodiazepine-4-carboxylate (prepared by analogy to WO 97/49690). Step 1E was carried out using 3(2,4-dichlorophenyl)-propionic acid and the 4methoxybenzyl group present in the product of Step 1E was removed using ceric ammonium nitrate under standard conditions.

($^1$H, CDCl$_3$) 2.71 (2H, m), 3.09 (2H, m), 5.23 (1H, d, J=7.8), 6.23 (1H, brs), 6.41 (1H, brs), 7.18 (5H, m), 7.35 (1H, d, J=1.9), 7.42 (1H, m), 7.50 (3H, m), 7.76 (2H, d, J=8.2), 9.3 (1H, s). MS(CI+): MH+=495

Example 6

(±)-4-[3-{[3-(2,4-chlorophenyl)propanoyl]amino}-1-(3-hydroxypropyl)-2-oxo-2,3-dihydro-1H-1,4-benzodiazepin-5-yl]benzamide Prepared by modification of the route shown in Scheme 1. The starting material for Step 1A was tert-butyl 1-(3-(tert-butyldiphenylsilyloxy)-propyl)-2,5-dioxo-1,2,3,5-tetrahydro-4H-1,4-benzodiazepine-4-carboxylate (prepared by analogy to WO 97/49690).

($^1$H, CDCl$_3$) 1.6 (1H, m), 1.8 (1H, m), 2.71 (2H, ddd, J=2.3, 7.6, 7.6), 3.09 (2H, dd, J=7.6, 7.6), 3.32 (1H, m), 3.38 (1H, m), 3.84 (1H, m), 4.51 (1H, m), 5.53 (1H, d, J=8), 5.60 (1H, brs), 6.0 (1H, brs), 6.45 (1H, brs), 7.16 (1H, m), 7.25 (3H, m), 7.37 (1H, d, J=2), 7.49–7.63 (5H, m), 7.82 (2H, d, J=8.2). MS(CI+): MH+=553

Example 7

(±)-3-(2,4-Dichlorophenyl)-1-N-[2-oxo-2,3-dihydro-1H-isoindol-5-yl)-1-methyl-2,3-dihydro-1H-1,4-benzodiazepin-3-yl]propanamide Prepared by the route shown in Scheme 3. Step 3E was carried out using 2-(1-oxo-2,3-dihydro-1H-isoindol-5-yl)-4,4,5,5-tetramethyl-1,3,2-dioxa-borolane.

($^1$H, CDCl$_3$) 9.26 (1H, d, J=8.1), 8.70 (1H, s), 7.75–7.34 (10H, m), 5.34 (1H, d, J=8.1), 4.43 (1H, d, J=12.0), 4.40 (1H, d, J=12.0), 3.39 (3H, s), 2.94–2.90 (2H, m), 2.65–2.61 (2H, m), MS (Electrospray): MH+=520

Example 8

(±)-3-(3,4-Dichlorophenyl)-1-N-[2-oxo-5-(1-oxo-1,2,3,4-tetrahydro-6-isoquinolinyl)-1-methyl-2,3-dihydro-1H-1,4-benzodiazepin-3-yl]propanamide Prepared by the route shown in Scheme 3. Step 3E was carried out using 2-(1-oxo-1,2,3,4-tetrahydro-6-isoquinolinyl)-4,4,5,5-tetramethyl-1,3,2-dioxa-borolane.

($^1$H, CDCl$_3$) 9.27 (1H, d, J=8.1), 8.03 (1H, s), 7.92 (1H, d, J=8.0), 7.77–7.34 (9H, m), 5.32 (1H, d, J=8.1), 3.40–3.35 (5H, m), 2.94–2.91 (4H, m), 2.67–2.62 (2H, m), MS (Electrospray): MH+=534

Example 9

4-[3-{[(3S)-3-phenylbutyryl]amino}-1-methyl-2-oxo-2,3-dihydro-1H-1,4-benzodiazepin-5-yl]benzamide (1:1 Mixture of Diastereomers)

Prepared by reaction of amine A and (S)-3-phenylbutyric acid using the procedure of Step 1E shown in Scheme 1.

($^1$H, CDCl$_3$) 1.36 (3H, d, J=6.9 Hz, single diast.), 1.38 (3H, d, J=7.0 Hz, single diast.), 2.61 (1H, m), 2.69 (1H, m), 3.37 (1H, m) 3.46 (3H, s, single diast.), 3.47 (3H, s, single diast.), 5.48 (1H, d, J=7.9 Hz, single diast.), 5.51 (1H, d, J=8.1 Hz, single diast.), 5.63 (1H, broad s), 6.12 (1H, broad s), 7.27 (2H, m), 7.29 (1H, m), 7.31 (2H, m), 7.33 (1H, m), 7.37 (2H, m), 7.40 (1H, m), 7.60 (3H, m), 7.82 (2H, m); MS(ES+), MH$^+$:455

Example 10

(±)-4-[3-{[3-(3,4-difluorophenyl)propanoyl]amino}-1-methyl-2-oxo-2,3-dihydro-1H-1,4-benzodiazepin-5-yl]benzamide Prepared by reaction of amine A and 3-(3,4-diflurophenyl)propionic acid using the procedure of Step 1E shown in Scheme 1.

($^1$H, CDCl$_3$) 2.67 (2H, m), 2.98 (2H, m), 3.48 (3H, s), 5.52 (1H, d, J=8.0 Hz), 5.61 (1H, broad s), 6.17 (1H, broad s), 6.93 (1H, m), 7.08 (2H, m), 7.28 (2H, m), 7.41 (2H, m) 7.61 (1H, m) 7.67 (2H, m), 7.82 (2H, m)

Example 11

(±)-4-[3-{[3-(3-chlorophenyl)propanoyl]amino}-1-methyl-2-oxo-2,3-dihydro-1H-1,4-benzodiazepin-5-yl]benzamide Prepared by reaction of amine A and 3-(3-chlorophenyl)propionic acid using the procedure of Step 1E shown in Scheme 1.

($^1$H, CDCl$_3$) 2.68 (2H, m), 2.98 (2H, m), 3.48 (3H, s), 5.53 (1H, d, J=7.9 Hz), 5.77 (1H, broad s), 6.21 (1H, broad s), 7.12 (1H, m), 7.17–7.29 (4H, m), 7.39 (3H, m), 7.59 (1H, m), 7.67 (2H, d, J=8.2 Hz), 7.83 (2H, d, J=8.2 Hz)

Example 12

(±)-4-[3-{[3-(4-fluorophenyl)propanoyl]amino}-1-methyl-2-oxo-2,3-dihydro-1H-1,4-benzodiazepin-5-yl]benzamide Prepared by reaction of amine A and 3-(4-fluorophenyl)propionic acid using the procedure of Step 1E shown in Scheme 1.

($^1$H, CDCl$_3$) 2.68 (2H, m), 2.99 (2H, m), 3.48 (1H, s), 5.53 (1H, d, J=8.0 Hz), 5.68 (1H, broad s), 6.12 (1H, broad s), 6.97 (2H, m), 7.19 (1H, m), 7.32 (1H, m), 7.39–7.45 (4H, m), 7.62 (1H, m), 7.68 (2H, m), 7.84 (2H, m); MS(ES+), MH$^+$:459

Example 13

(±)-4-[3-{[3-(4-chlorophenyl)propanoyl]amino}-1-methyl-2-oxo-2,3-dihydro-1H-1,4-benzodiazepin-5-yl]benzamide Prepared by reaction of amine A and 3-(4-chlorophenyl)propionic acid using the procedure of Step 1E shown in Scheme 1.

($^1$H, CDCl$_3$) 2.71 (2H, m), 3.03 (2H, m), 3.48 (3H, s), 5.54 (1H, d, J=8.0 Hz), 5.68 (1H, broad s), 6.16 (1H, broad s), 7.18 (2H, d, J=8.4 Hz), 7.25 (1H, m), 7.32 (1H, m), 7.39 (2H, m), 7.40 (2H, m), 7.59 (1H, m), 7.67 (2H, d, J=8.4 Hz), 7.83 (2H, d, J=8.4 Hz); MS(ES+), MH$^+$:475

Example 14

(±)-4-[3-{[3-phenylpropanoyl]amino}-1-methyl-2-oxo-2,3-dihydro-1H-1,4-benzodiazepin-5-yl]benzamide Prepared by reaction of amine A and 3-phenylpropionic acid using the procedure of Step 1E shown in Scheme 1.

($^1$H, CDCl$_3$) 2.68 (2H, m), 3.00 (2H, t, J=7.7 Hz), 3.48 (3H, s), 5.52 (1H, d, J=8.0 Hz), 5.65 (1H, broad s), 6.12 (1H, broad s), 7.19–7.41 (8H, m), 7.45 (1H, m), 7.61 (1H, m), 7.67 (2H, d, J=8.4 Hz), 7.83 (2H, d, J=8.4 Hz); MS(ES+), MH$^+$:441

Example 15

(±)-4-[3-{[3-(3,5-bis(trifluoromethyl)phenyl)propanoyl]amino}-1-methyl-2-oxo-2,3-dihydro-1H-1,4-benzodiazepin-5-yl]benzamide Prepared by reaction of amine A and 3-(3,5-bis(trifluoromethyl)phenyl)propionic acid using the procedure of Step 1E shown in Scheme 1.

($^1$H, CDCl$_3$) 2.75 (2H, m), 3.16 (2H, m), 3.48 (3H, s), 5.51 (1H, d, J=8.0 Hz), 5.65 (1H, broad s), 6.10 (1H, broad s), 7.24–7.42 (4H, m), 7.60–7.64 (6H, m), 7.82 (2H, d, J=8.4 Hz); MS(ES+), MH$^+$:577

Example 16

(±)-4-[3-{[3-(2,3-dichlorophenyl)propanoyl]amino}-1-methyl-2-oxo-2,3-dihydro-1H-1,4-benzodiazepin-5-yl]benzamide Prepared by reaction of amine A and 3-(2,3-dichlorophenyl)propionic acid using the procedure of Step 1E shown in Scheme 1.

($^1$H, CDCl$_3$) 2.72 (2H, m), 3.16 (2H, t, J=7.8 Hz), 3.48 (3H, s), 5.53 (1H, d, J=7.9 Hz), 5.90 (1H, broad s), 6.25 (1H, broad s), 7.10–7.46 (7H, m), 7.61 (1H, m), 7.66 (2H, d, J=8.3 Hz), 7.82 (2H, d, J=8.3 Hz); MS(ES+), MH$^+$:509

Example 17

(±)-4-[3-{[3-(3,4-dichlorophenyl)propanoyl]amino}-1-methyl-2-oxo-2,3-dihydro-1H-1,4-benzodiazepin-5-yl]benzamide Prepared by reaction of amine A and 3-(3,4-dichlorophenyl)propionic acid using the procedure of Step 1E shown in Scheme 1.

($^1$H, CDCl$_3$) 2.68 (2H, m), 2.98 (2H, m), 3.48 (3H, s), 5.51 (1H, d, J=8.0 Hz), 5.80 (1H, broad s), 6.15 (1H, broad s), 7.08 (1H, d, J=8.2 Hz), 7.24–7.41 (6H, m), 7.60 (1H, m), 7.66 (2H, d, J=8.2 Hz), 7.83 (2H, d, J=8.2 Hz); MS(ES+), MH$^+$:509

Example 18

(±)-4-[3-{[3-(2,4-dichlorophenyl)propanoyl]amino}-1-methyl-2-oxo-2,3-dihydro-1H-1,4-benzodiazepin-5-yl]benzamide Prepared by reaction of amine A and 3-(2,4-dichlorophenyl)propionic acid using the procedure of Step 1E shown in Scheme 1.

($^1$H, CDCl$_3$) 2.70 (2H, m), 3.11 (2H, m), 3.48 (3H, s), 5.52 (1H, d, J=8.0 Hz), 5.65 (1H, broad s), 6.05 (1H, broad s), 7.16 (1H, dd, J=8.2, 2.0 Hz), 7.24–7.41 (6H, m), 7.60 (1H, m), 7.67 (2H, d, J=8.2 Hz), 7.83 (2H, d, J=8.2 Hz); MS(ES+), MH$^+$:509

Example 19

(±)-4-[3-{[3-(3,5-dichlorophenyl)propanoyl]amino}-1-methyl-2-oxo-2,3-dihydro-1H-1,4-benzodiazepin-5-yl]benzamide Prepared by reaction of amine A and 3-(3,5-dichlorophenyl)propionic acid using the procedure of Step 1E shown in Scheme 1.

($^1$H; CDCl$_3$), 2.69 (2H, m), 2.97 (2H, m), 3.48 (3H, s), 5.52 (1H, d, J=8.0 Hz), 6.20 (2H, broad s), 7.12 (2H, m), 7.20–7.30 (3H, m), 7.40 (1H, d, J=8.3 Hz), 7.48 (1H, d, J=8 Hz), 7.61 (1H, m), 7.66 (2H, d, J=8.2 Hz), 7.83 (2H, d, J=8.2 Hz); MS(ES+), MH$^+$:509

Example 20

(±)-4-[3-{[3-(3-methoxyphenyl)propanoyl]amino}-1-methyl-2-oxo-2,3-dihydro-1H-1,4-benzodiazepin-5-yl]benzamide Prepared by reaction of amine A and 3-(3-methoxyphenyl)propionic acid using the procedure of Step 1E shown in Scheme 1.

($^1$H, CDCl$_3$) 2.70 (2H, m), 3.00 (2H, m), 3.48 (3H, s), 3.79 (3H, s), 5.54 (1H, d, J=8.0 Hz), 5.75 (1H, broad s), 6.20 (1H, broad s), 6.74–6.85 (3H, m), 7.19–7.41 (5H, m), 7.60 (1H, m), 7.67 (2H, d, J=8.2 Hz), 7.82 (2H, d, J=8.2 Hz); MS(ES+), MH$^+$:471

Example 21

(±)-4-[3-{[3-(4-methoxyphenyl)propanoyl]amino}-1-methyl-2-oxo-2,3-dihydro-1H-1,4-benzodiazepin-5-yl]benzamide Prepared by reaction of amine A and 3-(4-methoxyphenyl)propionic acid using the procedure of Step 1E shown in Scheme 1.

MS(ES+) MH$^+$:471

Example 22

(±)-4-[3-{[3-(4-methylphenyl)propanoyl]amino}-1-methyl-2-oxo-2,3-dihydro-1H-1,4-benzodiazepin-5-yl]benzamide Prepared by reaction of amine A and 3-(4-methylphenyl) propionic acid using the procedure of Step 1E shown in Scheme 1.

($^1$H, CDCl$_3$) 2.33 (3H, s), 2.68 (2H, m), 2.99 (2H, m), 3.48 (3H, s), 5.54 (1H, d, J=8.0 Hz), 5.73 (1H, broad s), 6.17 (1H, broad s), 7.10–7.15 (4H, m), 7.24–7.42 (4H, m), 7.60 (1H, m), 7.68 (2H, d, J=8.4 Hz), 7.83 (2H, d, J=8.4 Hz); MS(ES+), MH$^+$:455

Example 23

(±)-4-[3-{(2,4-dichlorophenoxyacetyl)amino}-1-methyl-2-oxo-2,3-dihydro-1H-1,4-benzodiazepin-5-yl]benzamide Prepared by reaction of amine A and 2,4-dichlorophenoxyacetic acid using the procedure of Step 1E shown in Scheme 1.

($^1$H, CDCl$_3$) 3.51 (3H, s), 4.63 (2H, Abq, J=36.4, 14.4 Hz), 5.59 (1H, d, J=7.8 Hz), 5.70 (1H, broad s), 6.12 (1H, broad s), 6.90 (1H, d, J=8.8 Hz), 7.22–7.45 (5H, m), 7.63 (1H, m), 7.70 (2H, d, J=8.4 Hz) 7.84 (2H, d, J=8.4 Hz) 8.67 (1H, d, J=7.71 Hz); MS(ES+), MH$^+$:511

Example 24

(±)-4-[3-{[3-(3,5-difluorophenyl)propanoyl]amino}-1-methyl-2-oxo-2,3-dihydro-1-1,4-benzodiazepin-5-yl]benzamide Prepared by reaction of amine A and 3-(3,5-difluorophenyl)propionic acid using the procedure of Step 1E shown in Scheme 1.

($^1$H, CDCl$_3$) 2.69 (2H, m), 3.01 (2H, m), 3.48 (3H, s), 5.54 (1H, d, J=7.8 Hz), 5.92 (1H, broad s), 6.28 (1H, broad s), 6.64 (1H, m), 6.77 (2H, d, J=6.3 Hz), 7.25–7.32 (2H, m), 7.41 (1H, d, J=8.3 Hz), 7.47 (1H, d, J=7.5 Hz), 7.63 (1H, m), 7.67 (2E, d, J=8.0 Hz), 7.83 (2H, d, J=8.0 Hz); MS(ES+), MH$^+$:477

Example 25

(±)-4-[3-{[3-(2,5-dichlorophenyl)propanoyl]amino}-1-methyl-2-oxo-2,3-dihydro-1H-1,4 benzodiazepin-5-yl]benzamide Prepared by reaction of amine A and 3-(2,5-dichlorophenyl)propionic acid using the procedure of Step 1E shown in Scheme 1.

($^1$H, CDCl$_3$) 2.70 (2H, m), 3.09 (2H, m), 3.48 (3H, s), 5.53 (1H, d, J=8.0 Hz), 5.76 (1H, broad s), 6.19 (1H, broad s), 7.14 (1H, dd, J=8.5, 2.5 Hz), 7.24–7.31 (4H, m), 7.40 (2H, dd, J=8.5, 2.3 Hz), 7.61 (1H, m), 7.68 (2H, d, J=8.2 Hz), 7.83 (2H, d, J=8.2 Hz); MS(ES+), MH$^+$:509

Example 26

(±)-4-[3-{[3-(2,4-dichlorophenoxy)propanoyl]amino}-1-methyl-2-oxo-2,3-dihydro-1H-1,4-benzodiazepin-5-yl]benzamide Prepared by reaction of amine A and 3-(2,4-dichlorophenoxy)propionic acid using the procedure of Step 1E shown in Scheme 1.

($^1$, (CDCl$_3$) 2.92 (2H, t, J=5.8 Hz), 3.48 (3H, s), 4.36 (2H, t, J=5.8 Hz), 5.55 (1H, d, J=7.8 Hz), 5.72 (1H, broad s), 6.18 (1H, broad s), 6.91 (1H, d, J=8.8 Hz), 7.16 (1H, dd, J=8.7, 2.4 Hz), 7.23–7.31 (3H, m), 7.35 (1H, d, J=2.6 Hz), 7.40 (2H, dd, J=8.1, 0.5 Hz), 7.61 (1H, m), 7.68 (2H, d, J=8.2 Hz), 7.83 (2H, d, J=8.2 Hz); MS(ES+), MH$^+$:525

Example 27

(±)-4-[3-{[2-(3,4-dichlorophenoxy)acetyl]amino}-1-methyl-2-oxo-2,3-dihydro-1H-4-benzodiazepin-5-yl] benzamide Prepared by reaction of amine A and 3,4-dichlorophenoxyacetic acid using the procedure of Step 1E shown in Scheme 1.

($^1$H, CDCl$_3$) 3.48 (3H, s), 4.59 (2H, dd, J=24.8, 14.7 Hz), 5.59 (1H, d, J=8.0 Hz), 5.77 (1H, broad s), 6.19 (1H, broad s), 6.89 (1H, dd, J=8.9, 3.0 Hz), 7.13 (1H, d, J=3.0 Hz), 7.27–7.44 (4H, m), 7.63 (1H, m), 7.69 (2H, d, J=8.3 Hz), 7.83 (2H, d, J=8.3 Hz), 8.36 (1H, d, J=8.0 Hz); MS(ES+), MH$^+$:511

The invention claimed is:

1. A compound of formula I:

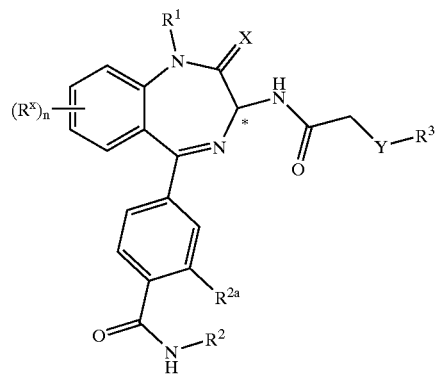

wherein
n is 0–3;
each $R^x$ independently represents halogen, —CN, —NO$_2$, $C_{1-6}$alkyl, polyfluoroC$_{1-6}$alkyl, —OH or C$_{1-4}$alkoxy;
X represents O, S or N—$R^a$ where $R^a$ together with $R^1$ completes a fused imidazole or 4,5-dihydroimidazole ring;
Y represents —CH$_2$—, —CH(OH)—, —CH(CH$_3$)—, —CH$_2$O—, —O— or —S;
$R^1$ represents H, $C_{1-6}$alkyl, $C_{3-8}$cycloalkyl, $C_{2-6}$alkenyl, $C_{2-6}$alkynyl or polyfluoroC$_{1-6}$alkyl, said alkyl, cycloalkyl, alkenyl and alkynyl groups being optionally substituted by halogen, —CN, —NO$_2$, aryl, heteroaryl, —COR$^6$, —CO$_2$R$^6$, —CON(R$^6$)$_2$, —OCOR$^7$, —NR$^6$COR$^7$, —NR$^6$SO$_2$R$^7$, —SO$_3$R$^6$, —SO$_2$N(R$^6$)$_2$, —OR$^6$, —SR$^6$ or —N(R$^6$)$_2$; or when X is N—$R^a$, $R^1$ together with $R^a$ completes a fused imidazole or 4,5-dihydroimidazole ring;
$R^2$ and $R^{2a}$ each represents hydrogen, or $R^2$ and $R^{2a}$ together complete a fused lactam ring of 4–7 members;
$R^3$ represents aryl, heteroaryl, $C_{1-6}$alkyl, polyfluoroC$_{1-6}$alkyl, $C_{3-8}$cycloalkyl or $C_{3-8}$cycloalkylC$_{1-6}$alkyl;
each $R^6$ independently represents H, polyfluoroC$_{1-6}$alkyl, or $C_{1-6}$alkyl which is optionally substituted with halogen, —CN, —NO$_2$, —OH, —SH, —NH$_2$, phenyl, $C_{1-4}$alkoxy, $C_{1-4}$alkylthio, $C_{1-4}$alkylamino, di($C_{1-4}$alkyl)amino, —CO$_2$H, —CO$_2$C$_{1-4}$alkyl, —CONH$_2$, —CONHC$_{1-4}$alkyl or —CON(C$_{1-4}$alkyl)$_2$; or two $R^6$ groups attached to a single nitrogen atom may complete a heterocyclic ring of from 3 to 12 members including the said nitrogen, the remaining atoms being selected from C, N, O and S, and the ring optionally bearing up to 3 substituents independently selected from $C_{1-6}$alkyl, polyfluoroC$_{1-6}$alkyl, $C_{2-7}$acyl, —OH and —CONH$_2$;
$R^7$ represents $R^6$ that is other than H;
"aryl" refers to phenyl which is optionally fused to a 5–7 membered saturated or unsaturated ring which may be carbocyclic or may comprise up to 3 heteroatoms selected from nitrogen, oxygen and sulphur, and which may be oxo-substituted, said phenyl and optional fused ring together bearing 0–3 substituents independently selected from $C_{1-6}$alkyl [which is optionally substituted with halogen, —CN, —NO$_2$, —OH, —SH, —NH$_2$, $C_{1-4}$alkoxy, $C_{1-4}$alkylthio, $C_{1-4}$alkylamino, di($C_{1-4}$alkyl)amino, —CO$_2$H, —CO$_2$C$_{1-4}$alkyl, —CONH$_2$, —CONHC$_{1-4}$alkyl or —CON(C$_{1-4}$alkyl)$_2$], polyfluoroC$_{1-6}$alkyl, halogen, —CN, —NO$_2$, heteroaryl, —COR$^6$, —CO$_2$R$^6$, —CON(R$^6$)$_2$, —OCOR$^7$, —NR$^6$COR$^7$, —NR$^6$SO$_2$R$^7$, —SO$_3$R$^6$, —SO$_2$N(R$^6$)$_2$, —OR$^6$, —SR$^6$ and —N(R$^6$)$_2$;
"heteroaryl" refers to a heteroaromatic ring of 5 or 6 members, at least one member being nitrogen, oxygen or sulphur and the remainder carbon, said ring optionally being fused to a 5–7 membered saturated or unsaturated ring which may be carbocyclic or may comprise up to 3 heteroatoms selected from nitrogen, oxygen and sulphur, and which may be oxo-substituted heteroaromatic ring and optional fused ring together bearing 0–3 substituents independently selected from $C_{1-6}$alkyl [which is optionally substituted with halogen, —CN, —NO$_2$, —OH, —SH, —NH$_2$, $C_{1-4}$alkoxy, $C_{1-4}$alkylthio, $C_{1-4}$alkylamino, di($C_{1-4}$alkyl)amino, —CO$_2$H, —CO$_2$C$_{1-4}$alkyl, —CONH$_2$, —CONHC$_{1-4}$alkyl or —CON(C$_{1-4}$alkyl)$_2$], polyfluoroC$_{1-6}$alkyl, halogen, —CN, —NO$_2$, phenyl, —COR$^6$, —CO$_2$R$^6$, —CON(R$^6$)$_2$, —OCOR$^7$, —NR$^6$COR$^7$, —NR$^6$SO$_2$R$^7$, —SO$_3$R$^6$, —SO$_2$N(R$^6$)$_2$, —OR$^6$, SR$^6$ and —N(R$^6$)$_2$;
or a pharmaceutically acceptable salt thereof.

2. A compound according to claim 1 wherein the stereochemistry at the position marked with an asterisk (*) in formula I is as shown in formula Ia:

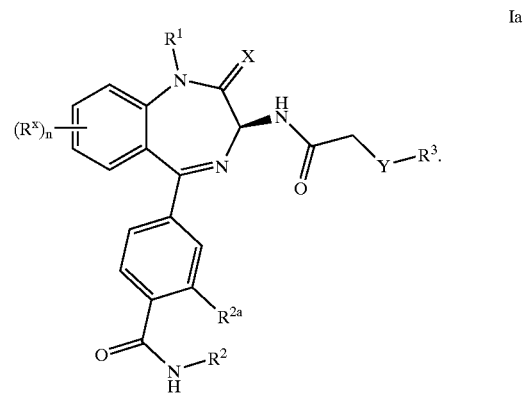

Ia

3. A compound according to claim 1 of formula II:

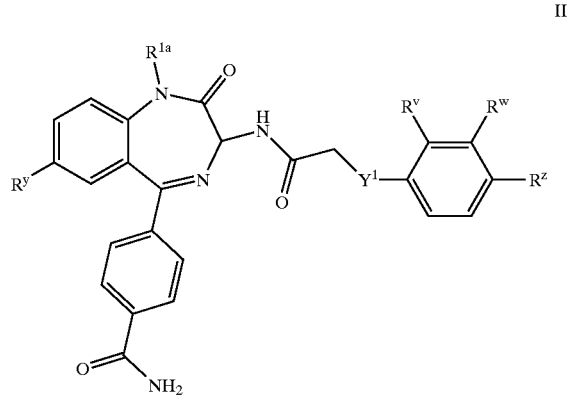

II wherein:
$R^y$, $R^z$, $R^v$ and $R^w$ are independently H or halogen;
$Y^1$ is —CH$_2$, —CH(OH)—, —CH(CH$_3$)—, —CH$_2$O— or —O—; and
$R^{1a}$ is H, polyfluoroC$_{1-4}$alkyl, or C$_{-4}$alkyl which is optionally substituted by —OH, —CN, carbamoyl or dimethylamino;
or a pharmaceutically acceptable salt thereof.

4. A compound according to claim 1 of formula III:

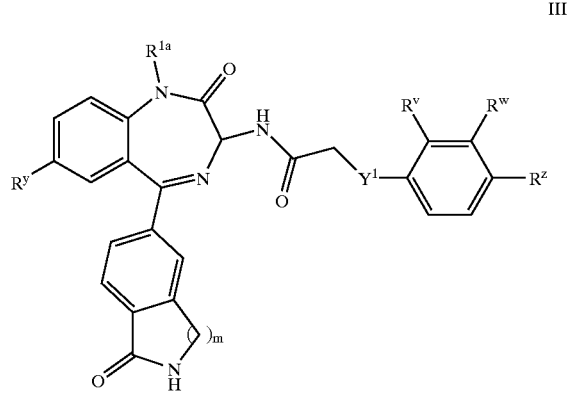

III wherein:

m is 1 or 2;

$R^y$, $R^z$, $R^v$ and $R^w$ are independently H or halogen;

$Y^1$ is —$CH_2$—, —CH(OH)—, —CH($CH_3$)—, —$CH_2$O— or —O—; and $R^{1a}$ is H, polyfluoro$C_{1-4}$alkyl, or $C_{1-4}$alkyl which is optionally substituted by —OH, —CN, carbamoyl or dimethylamino;

or a pharmaceutically acceptable salt thereof.

5. A compound according to claim 3 or claim 4 wherein $R^z$, halogen and one of $R^v$ and $R^w$ is H while the other is halogen.

6. A compound according to claim 1 selected from:
- (±)-4-[3-{[3-(2,4-dichlorophenyl)propanoyl]amino}-1-(3-[morpholin-4-yl]propyl)-2-oxo-2,3-dihydro-1H-1,4-benzodiazepin-5-yl]benzamide;
- (±)-4-[3-{[3-(2,4-dichlorophenyl)propanoyl]amino}-2-oxo-1-(3-[pyrrolidin-1-y]propyl)-2,3-dihydro-1H-1,4-benzodiazepin-5-yl]benzamide hydrochloride;
- (±)-4-[3-{[3-(2,4-dichlorophenyl)propanoyl]amino}-1-[3-(dimethylamino)propyl]-2-oxo-2,3-dihydro-1H-1,4-benzodiazepin-5-yl]benzamide hydrochloride;
- (±)-4-[3-{[3-(2,4-dichlorophenyl)propanoyl]amino}-1-(4-methoxybenzyl)-2-oxo-2,3-dihydro-1H-1,4-benzodiazepin-5-yl]benzamide;
- (±)-4-(3-{[3-(2,4-dichlorophenyl)propanoyl]amino}-2-oxo-2,3-dihydro-1H-1,4-benzodiazepin-5-yl)benzamide;
- (±)-4-[3-{[3-(2,4-dichlorophenyl)propanoyl]amino}-1-(3-hydroxypropyl)-2-oxo-2,3-dihydro-1H-1,4-benzodiazepin-5-yl]benzamide;
- (±)-3-(2,4-dichlorophenyl)-1-N-[2-oxo-5-(1-oxo-2,3-dihydro-1H-isoindol-5-yl)-1-methyl-2,3-dihydro-1H-1,4-benzodiazepin-3-yl]propanamide;
- (±)-3-(3,4-dichlorophenyl)-1-N-[2-oxo-5-(1-oxo-1,2,3,4-tetrahydro-6-isoquinolinyl)-1-methyl-2,3-dihydro-1H-1,4-benzodiazepin-3-yl]propanamide;
- 4-[3-{[(3S)-3-phenylbutyryl]amino}-1-methyl-2-oxo-2,3-dihydro-1H-1,4-benzodiazepin-5-yl]benzamide;
- (±)-4-[3-{[3-(3,4-difluorophenyl)propanoyl]amino}-1-methyl-2-oxo-2,3-dihydro-1H-1,4-benzodiazepin-5-yl]benzamide;
- (±)-4-[3-{[3-(3-chlorophenyl)propanoyl]amino}-1-methyl-2-oxo-2,3-dihydro-1H-1,4-benzodiazepin-5-yl]benzamide;
- (±)-4-[3-{[3-(4-fluorophenyl)propanoyl]amino}-1-methyl-2-oxo-2,3-dihydro-1H-1,4-benzodiazepin-5-yl]benzamide;
- (±)-4-[3-{[3-(4-chlorophenyl)propanoyl]amino}-1-methyl-2-oxo-2,3-dihydro-1H-1,4-benzodiazepin-5-yl]benzamide;
- (±)-4-[3-{[3-phenylpropanoyl]amino}-1-methyl-2-oxo-2,3-dihydro-1H-1,4-benzodiazepin-5-yl]benzamide;
- (±)-4-[3-{[3-(3,5-bis(trifluoromethyl)phenyl)propanoyl]amino}-1-methyl-2-oxo-2,3-dihydro-1H-1,4-benzodiazepin-5-yl]benzamide;
- (±)-4-[3-{[3-(2,3-dichlorophenyl)propanoyl]amino}-1-methyl-2-oxo-2,3-dihydro-1H-1,4-benzodiazepin-5-yl]benzamide;
- (±)-4-[3-{[3-(3,4-dichlorophenyl)propanoyl]amino}-1-methyl-2-oxo-2,3-dihydro-1H-1,4-benzodiazepin-5-yl]benzamide;
- (±)-4-[3-{[3-(2,4-dichlorophenyl)propanoyl]amino}-1-methyl-2-oxo-2,3-dihydro-1H-1,4-benzodiazepin-5-yl]benzamide;
- (±)-4-[3-{[3-(3,5-dichlorophenyl)propanoyl]amino}-1-methyl-2-oxo-2,3-dihydro-1H-1,4-benzodiazepin-5-yl]benzamide;
- (±)-4-[3-{[3-(3-methoxyphenyl)propanoyl]amino}-1-methyl-2-oxo-2,3-dihydro-1H-1,4-benzodiazepin-5-yl]benzamide;
- (±)-4-[3-{[3-(4-methoxyphenyl)propanoyl]amino}-1-methyl-2-oxo-2,3-dihydro-1H-1,4-benzodiazepin-5-yl]benzamide;
- (±)-4-[3-{[3-(4-methylphenyl)propanoyl]amino}-1-methyl-2-oxo-2,3-dihydro-1H-1,4-benzodiazepin-5-yl]benzamide;
- (±)-4-[3-{(2,4-dichlorophenoxy)acetyl]amino}-1-methyl-2-oxo-2,3-dihydro-1H-1,4-benzodiazepin-5-yl]benzamide;
- (±)-4-[3-{[3-(3,5-difluorophenyl)propanoyl]amino}-1-methyl-2-oxo-2,3-dihydro-1H-1,4-benzodiazepin-5-yl]benzamide;
- (±)-4-[3-{[3-(2,5-dichlorophenyl)propanoyl]amino}-1-methyl-2-oxo-2,3-dihydro-1H-1,4-benzodiazepin-5-yl]benzamide;
- (±)-4-[3-{[3-(2,4-dichlorophenoxy)propanoyl]amino}-1-methyl-2-oxo-2,3-dihydro-1H-1,4-benzodiazepin-5-yl]benzamide;
- (±)-4-[3-{[2-(3,4-dichlorophenoxy)acetyl]amino}-1-methyl-2-oxo-2,3-dihydro-1H-1,4-benzodiazepin-5-yl]benzamide.

7. A pharmaceutical composition comprising one or more compounds according to claim 1 and a pharmaceutically acceptable carrier.

8. A method of treatment of a subject suffering from Alzheimer's disease which comprises administering to that subject an effective amount of a compound according to claim 1.

* * * * *

UNITED STATES PATENT AND TRADEMARK OFFICE
CERTIFICATE OF CORRECTION

PATENT NO. : 6,995,155 B2  
APPLICATION NO. : 10/399231  
DATED : February 7, 2006  
INVENTOR(S) : Ian Churcher, Alan John Nadin and Andrew Pate Owens It is certified that error appears in the above-identified patent and that said Letters Patent is hereby corrected as shown below:

Title page,
Item [22], PCT Filed, delete "Aug. 8, 2001" and replace with -- Oct 8, 2001 --.

Signed and Sealed this

Thirteenth Day of February, 2007

JON W. DUDAS  
*Director of the United States Patent and Trademark Office*